US010888530B2

(12) United States Patent
Schwartz et al.

(10) Patent No.: US 10,888,530 B2
(45) Date of Patent: Jan. 12, 2021

(54) IMPLANTABLE DRUG DELIVERY COMPOSITIONS AND METHODS OF USE THEREOF

(71) Applicant: AcuityBio Corporation, Newton, MA (US)

(72) Inventors: John Schwartz, Newton, MA (US); Aaron Henry Colby, Concord, MA (US)

(73) Assignee: AcuityBio Corporation, Newtonville, MA (US)

( * ) Notice: Subject to any disclaimer, the term of this patent is extended or adjusted under 35 U.S.C. 154(b) by 0 days.

(21) Appl. No.: 15/845,902

(22) Filed: Dec. 18, 2017

(65) Prior Publication Data
US 2018/0193282 A1 Jul. 12, 2018

Related U.S. Application Data

(63) Continuation of application No. PCT/US2016/038080, filed on Jun. 17, 2016.

(60) Provisional application No. 62/181,707, filed on Jun. 18, 2015.

(51) Int. Cl.
A61K 9/00 (2006.01)
A61L 31/16 (2006.01)
A61P 35/00 (2006.01)
A61K 9/70 (2006.01)
A61L 27/36 (2006.01)
A61L 31/10 (2006.01)
A61L 31/14 (2006.01)
A61L 27/54 (2006.01)
A61L 27/56 (2006.01)
A61L 27/34 (2006.01)
A61L 27/18 (2006.01)
A61L 31/06 (2006.01)
A61L 27/58 (2006.01)
A61K 31/337 (2006.01)
A61K 47/34 (2017.01)
A61K 47/46 (2006.01)

(52) U.S. Cl.
CPC ............ A61K 9/70 (2013.01); A61K 9/007 (2013.01); A61K 9/0024 (2013.01); A61K 31/337 (2013.01); A61K 47/34 (2013.01); A61K 47/46 (2013.01); A61L 27/18 (2013.01); A61L 27/34 (2013.01); A61L 27/3604 (2013.01); A61L 27/54 (2013.01); A61L 27/56 (2013.01); A61L 27/58 (2013.01); A61L 31/06 (2013.01); A61L 31/10 (2013.01); A61L 31/148 (2013.01); A61L 31/16 (2013.01); A61P 35/00 (2018.01); A61L 2300/416 (2013.01); A61L 2300/602 (2013.01)

(58) Field of Classification Search
CPC ..... A61P 35/00; A61K 2300/00; A61K 45/06; A61L 2300/416; A61L 31/041; A61L 27/3604
See application file for complete search history.

(56) References Cited

U.S. PATENT DOCUMENTS

| 5,543,156 | A | 8/1996 | Roorda et al. |
| 5,626,862 | A | 5/1997 | Brem et al. |
| 5,651,986 | A | 7/1997 | Brem et al. |
| 5,759,583 | A * | 6/1998 | Iwamoto ............... A61K 9/1617 424/502 |
| 5,846,565 | A | 12/1998 | Brem et al. |
| 5,886,026 | A | 3/1999 | Hunter et al. |
| 6,110,484 | A * | 8/2000 | Sierra ................... A61L 27/225 424/422 |
| RE37,410 | E | 10/2001 | Brem et al. |
| 6,544,544 | B2 | 4/2003 | Hunter et al. |
| 8,221,794 | B2 | 7/2012 | Hunter et al. |
| 2003/0203000 | A1* | 10/2003 | Schwarz ................. A61L 31/16 424/423 |
| 2005/0004158 | A1* | 1/2005 | Iyer .................... A61B 17/0057 514/291 |
| 2006/0204441 | A1* | 9/2006 | Atala .................. A61K 41/0042 424/9.6 |
| 2007/0141112 | A1 | 6/2007 | Falotico et al. |
| 2008/0020063 | A1 | 1/2008 | Hunter et al. |
| 2010/0278725 | A1 | 11/2010 | Liu et al. |
| 2012/0209381 | A1 | 8/2012 | Powell et al. |
| 2012/0273993 | A1* | 11/2012 | Shoseyov ............... A61L 27/24 264/202 |
| 2013/0281977 | A1 | 10/2013 | Steele et al. |
| 2014/0178455 | A1* | 6/2014 | Nukavarapu .......... A61L 27/58 424/426 |
| 2014/0193569 | A1* | 7/2014 | Huang ................... A61L 31/08 427/2.25 |
| 2015/0025106 | A1 | 1/2015 | Kwon et al. |

FOREIGN PATENT DOCUMENTS

| AU | 2007/254682 A1 | 1/2008 |
| CN | 101264346 A | 9/2008 |
| WO | 02/045689 A1 | 6/2002 |
| WO | 2009/140131 A2 | 11/2009 |
| WO | 2012/091680 A1 | 7/2012 |
| WO | WO-2014052724 A1 * | 4/2014 ............. A61L 27/18 |

OTHER PUBLICATIONS

Chen et al. A novel drug-eluting stent spray-coated with multi-layers of collagen and sirolimus. J Control Release. 108 (1):178-89 (2005).
Huang et al. The influence of additives in modulating drug delivery and degradation of PLGA thin films. NPG Asia Materials 5(e54): 1-11 (2013).
Klose et al. PLGA-based drug delivery systems: importance of the type of drug and device geometry. Int J Pharm. 354 (1-2):95-103 (2008).

(Continued)

Primary Examiner — Tracy Liu
(74) Attorney, Agent, or Firm — McCarter & English, LLP

(57) ABSTRACT

Provided herein are implantable compositions and methods of use thereof for the local delivery of therapeutically active agents.

8 Claims, 21 Drawing Sheets

(56) References Cited

OTHER PUBLICATIONS

Li et al. Pharmacokinetic profile of paclitaxel in the plasma, lung, and diaphragm following intravenous or intrapleural administration in rats. Thorac Cancer. 6(1):43-8 (2015).

Liu et al. A novel trans-lymphatic drug delivery system: implantable gelatin sponge impregnated with PLGA-paclitaxel microspheres. Biomaterials. 28(21):3236-44 (2007).

Liu et al. Targeting colloidal particulates to thoracic lymph nodes. Lung Cancer. 51(3):377-86 (2006).

Liu et al. Translymphatic chemotherapy by intrapleural placement of gelatin sponge containing biodegradable Paclitaxel colloids controls lymphatic metastasis in lung cancer. Cancer Res. 69(3):1174-81 (2009).

Schrump et al. Pharmacokinetics of paclitaxel administered by hyperthermic retrograde isolated lung perfusion techniques. J Thorac Cardiovasc Surg. 123(4):686-94, Abstract Only (2002).

Steele et al. The effect of polyethylene glycol structure on paclitaxel drug release and mechanical properties of PLGA thin films. Acta Biomater. 7(5):1973-83 (2011).

Steele et al. Tuning drug release in polyester thin films: terminal end-groups determine specific rates of additive-free controlled drug release. NPG Asia Materials 5(e46): 1-8 (2013).

Steendam. (2005) SynBiosys™ Biodegradable Polymeric Drug Delivery System. Business Briefing: Pharma Outsourcing.

Wang et al. Controlled release of sirolimus from a multilayered PLGA stent matrix. Biomaterials. 27(32):5588-95 (2006).

Downey et al. Functional comparison of staple line reinforcements in lung resection. Ann Thorac Surg. 82(5):1880-3 (2006).

Kang et al. Paclitaxel distribution in poly(ethylene glycol)/poly(lactide-co-glycolic acid) blends and its release visualized by coherent anti-Stokes Raman scattering microscopy. J Control Release. 122(3):261-8 (2007).

Liu et al. Prevention of local tumor recurrence following surgery using low-dose chemotherapeutic polymer films. Ann Surg Oncol. 17(4): 1203-13 (2010).

Pavlinich et al. In vitro drug release and hemocompatibility of biodegradable Plga/Peg coated paclitaxel-eluting stents. Advanced Materials Research. 651:49-53 (2013).

Wolinsky et al. Prevention of in vivo lung tumor growth by prolonged local delivery of hydroxycamptothecin using poly (ester-carbonate)-collagen composites. J Control Release. 144(3):280-7 (2010).

Ueda et al. Sutureless pneumostasis using bioabsorbable mesh and glue during major lung resection for cancer: who are the best candidates? J Thorac Cardiovasc Surg. 139(3):600-5 (2010).

\* cited by examiner

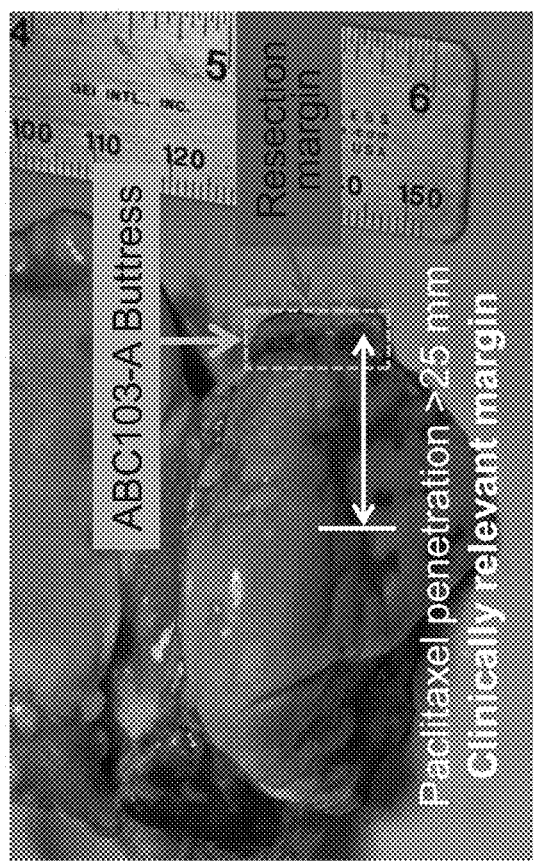
FIG. 2A
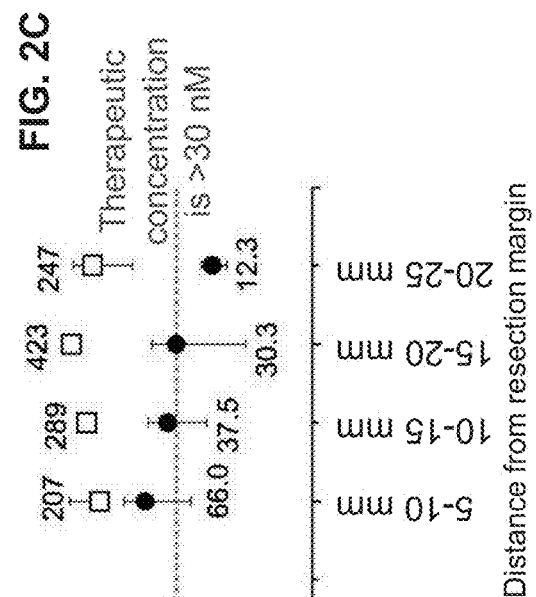
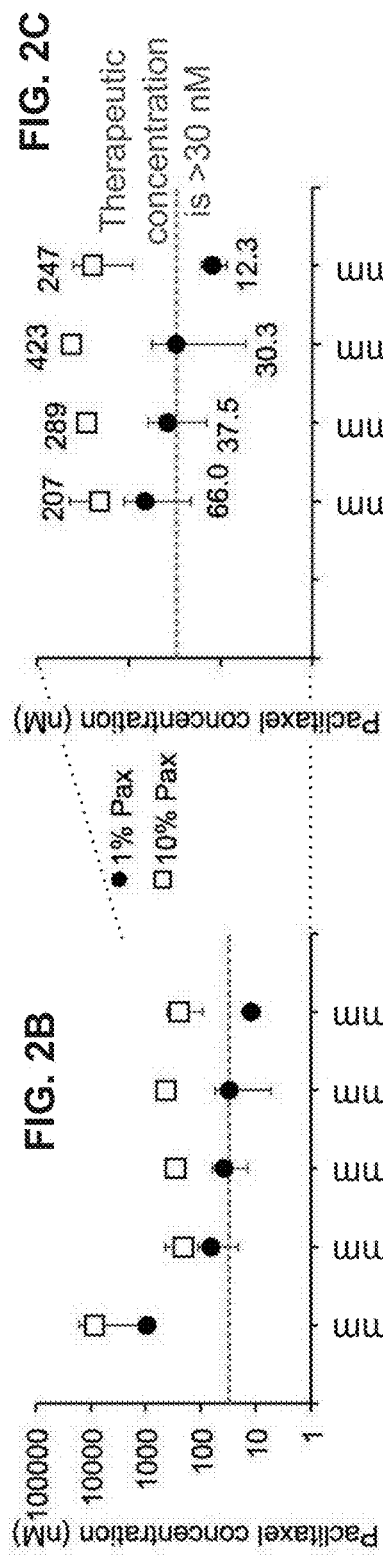
Paclitaxel concentration v. penetration depth from resection margin

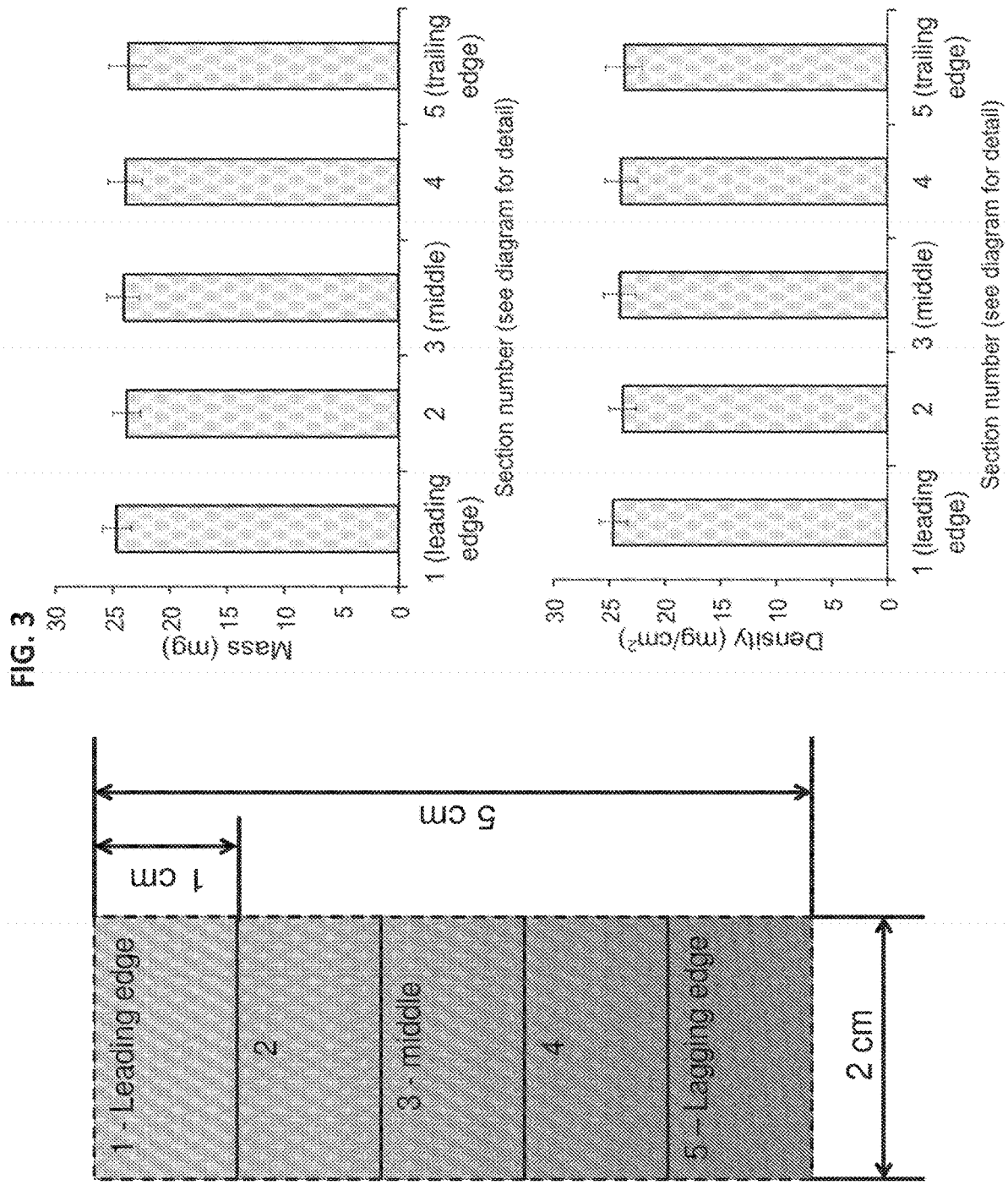

Left column – with EtO    Right column – without EtO
FIG. 8A
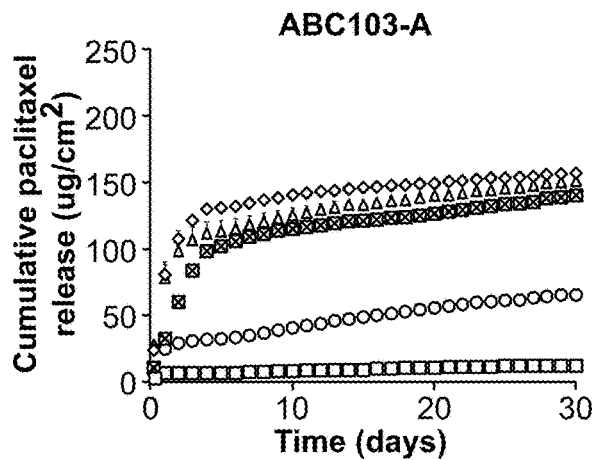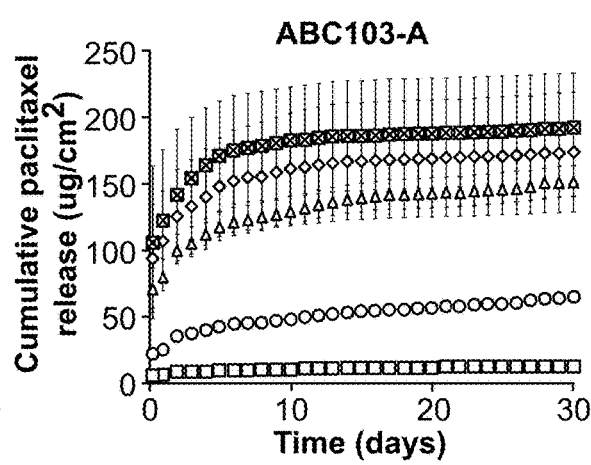
FIG. 8B
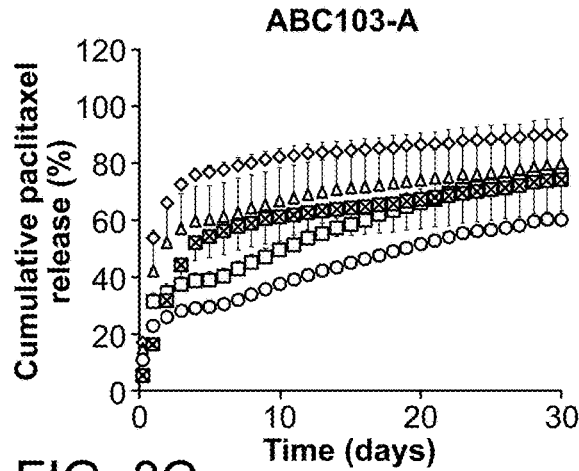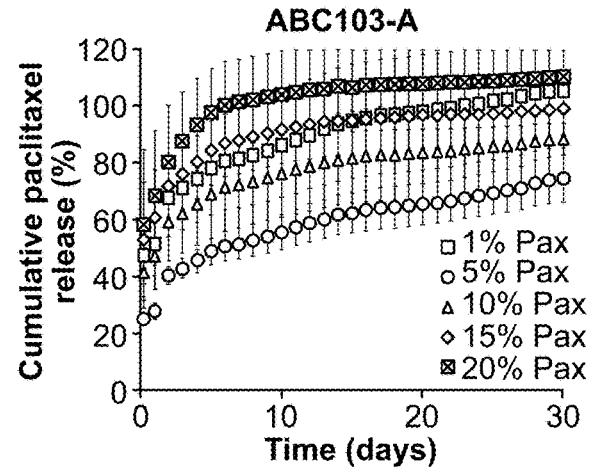
FIG. 8C
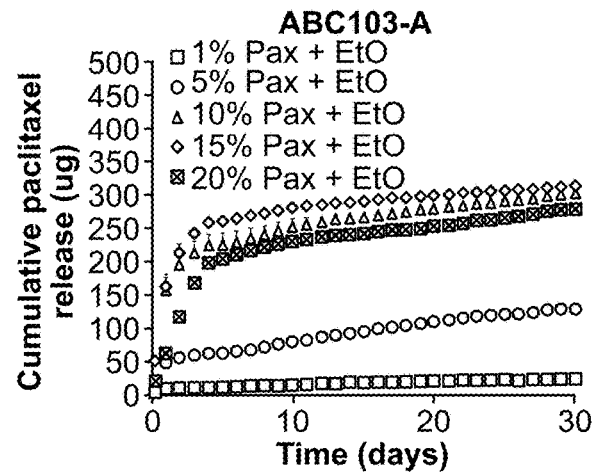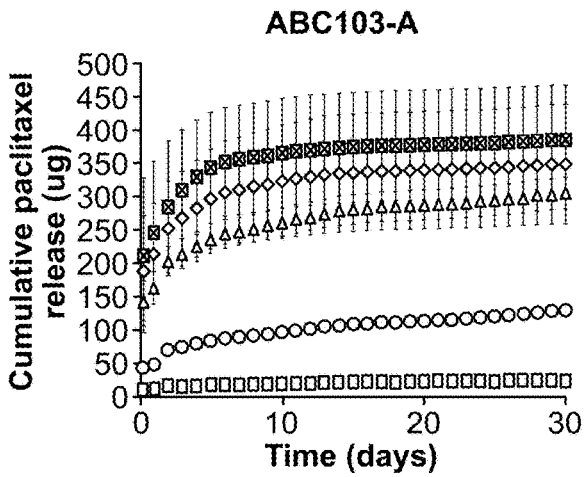

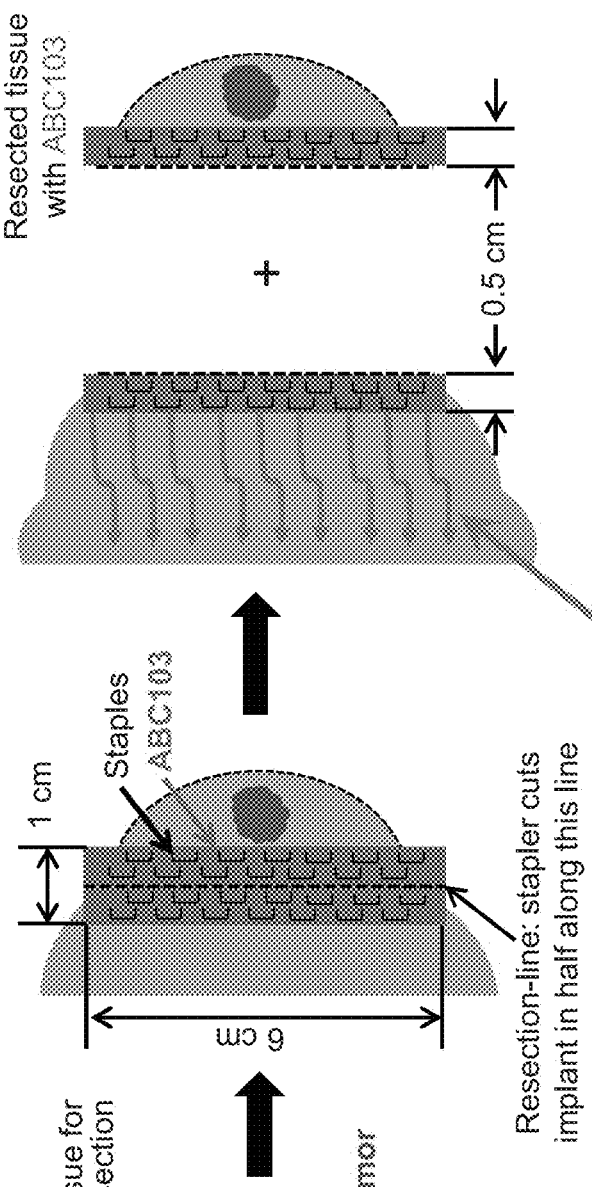
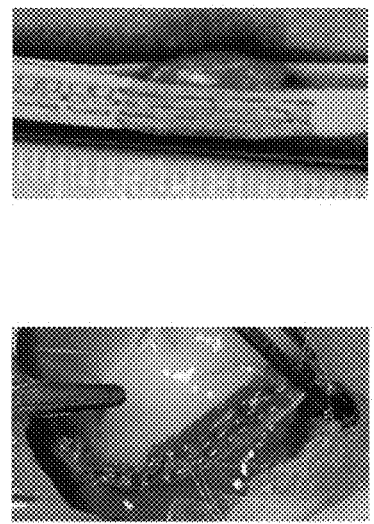
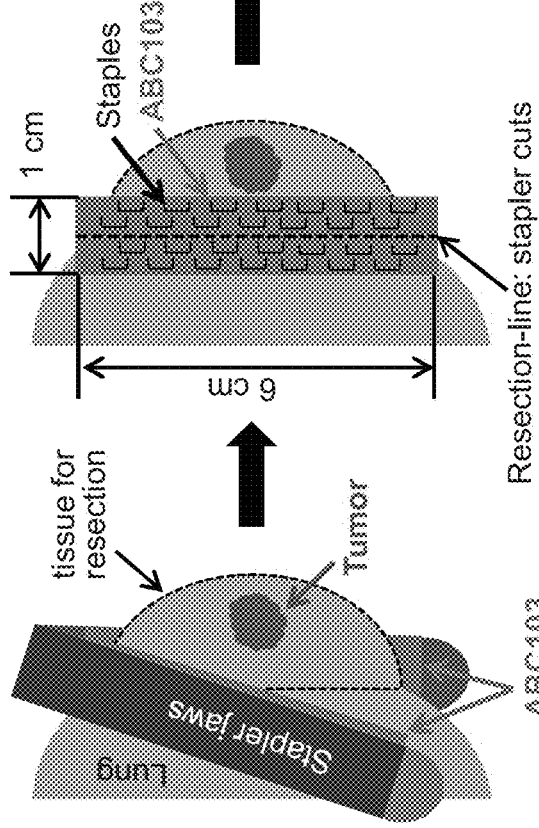
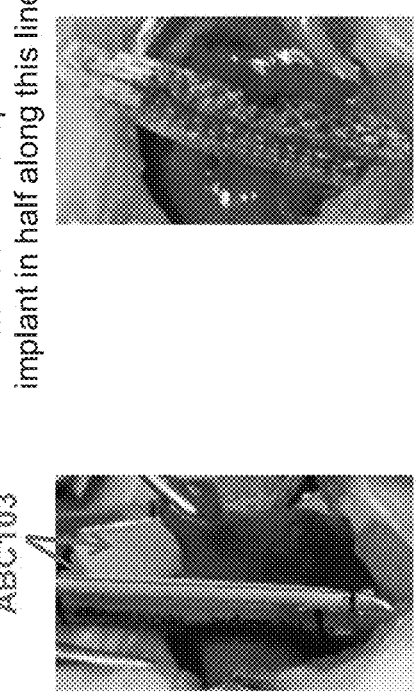
FIG. 13A Tissue is clamped between stapler jaws
FIG. 13B Staples are deployed and implant / tissue cut
FIG. 13C Remaining lung tissue with ABC103
FIG. 13D Resected tissue with ABC103
Paclitaxel is locally delivered up to 8 cm from the resection margin FIG. 14A Uncoated buttress FIG. 14B ABC103-A without paclitaxel FIG. 14C ABC103-A with 225 ug/cm² paclitaxel
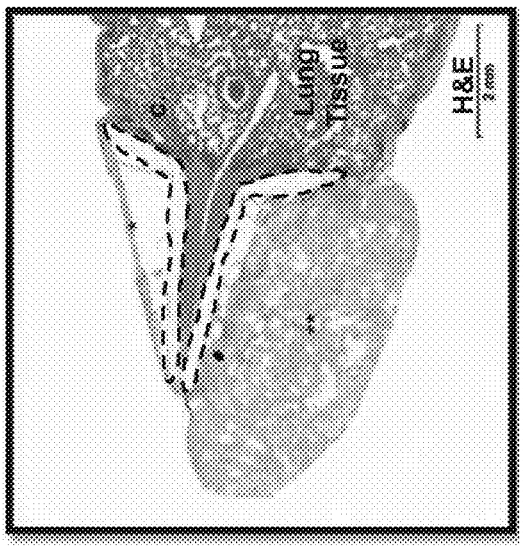
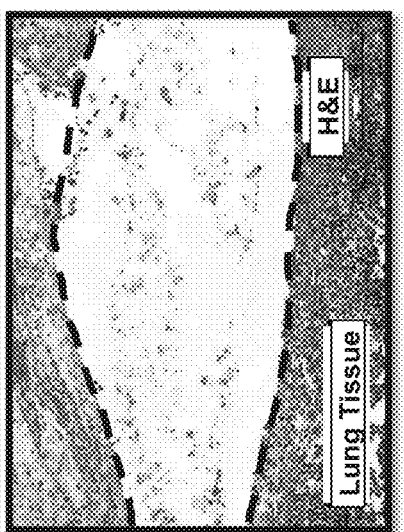
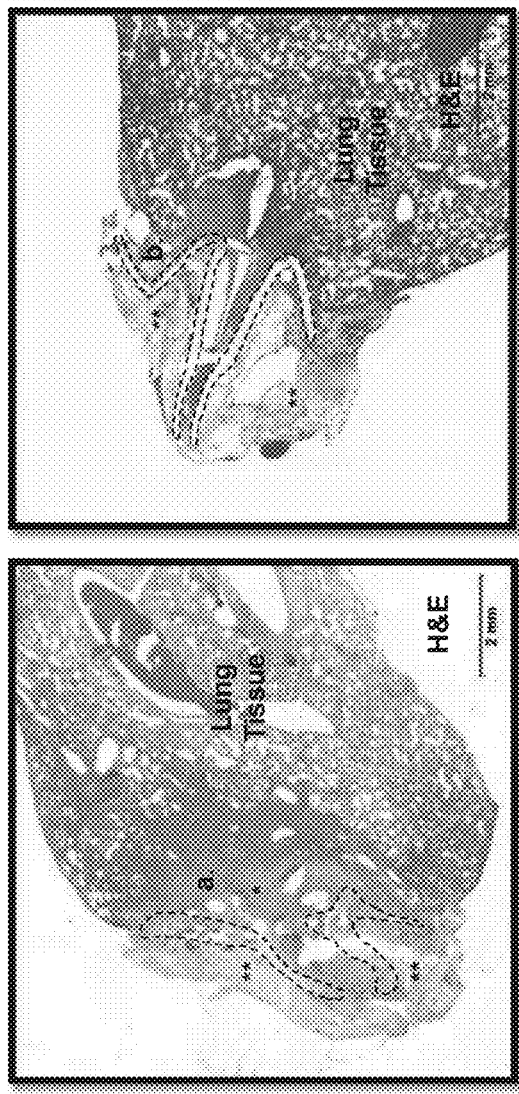
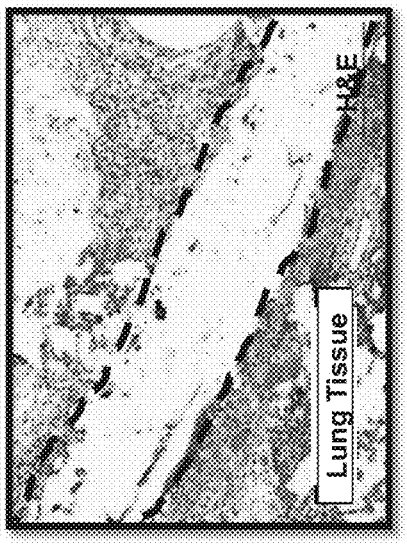

Distribution of paclitaxel from ABC103 implanted orthotopically in pig lung

IMPLANTABLE DRUG DELIVERY COMPOSITIONS AND METHODS OF USE THEREOF

RELATED APPLICATIONS

This application is a continuation of international application No. PCT/US2016/038080, filed Jun. 17, 2016, which claims the benefit of U.S. Provisional Application No. 62/181,707, filed Jun. 18, 2015, the entire contents of each of which are incorporated herein by reference.

BACKGROUND OF THE INVENTION

The sustained delivery of pharmaceutical agents providing efficacy with low systemic toxicity is desirable for the treatment of diseases including, but not limited to, malignancy and certain infections. Medication can be administered in a variety of ways including orally, aerosolized inhaled, subcutaneously, intramuscularly, intraperitoneally, transcutaneously, intrathoracically and intravenously.

Drug delivery refers to approaches, formulations, technologies, and systems for transporting a pharmaceutical compound in the body as needed to safely achieve a desired therapeutic effect. Conventional drug delivery may involve site-targeting within the body or facilitating systemic pharmacokinetics. In either case, conventional drug delivery is typically concerned with both quantity and duration of drug presence.

Unfortunately, systemic administration of drugs can result in unwanted toxicity. Toxicity resulting from the systemic administration of many drugs is often related to total systemic drug exposure at certain concentrations. Intravenous and systemic drug therapy most commonly fail due to one or more of the following: poor drug solubility, toxicity, short in-vivo stability of drug, unfavorable drug pharmacokinetics, poor biodistribution, poor bioavailability, rapid metabolism and excretion and lack of selectivity for the disease target.

Variability in how individual patients absorb the drug into plasma and clear the drug from systemic circulation may account for a significant component of patient-to-patient differences in toxicity and differences in toxicity for an individual patient from day-to-day. Pharmacokinetic variability may result from day-to-day changes in an individual patient's ability to metabolize or excrete drug, or from between-patient differences in drug metabolism or excretion. Generally, drugs administered intravenously (i.e., through IV) have a relatively limited half-life due to clearance from plasma through protein binding and excretion. The concentration of drug that needs to be administered systemically to be effective is typically constrained by the maximum tolerated dose or rate of administration due to systemic side effects. This limitation reduces the possibility of delivering a sustained and efficacious drug level due to dose limiting toxicity.

In vivo drug concentration is commonly measured in blood. Most drugs require a minimum effective plasma concentration and duration of this concentration for the drug's effects to be manifest. Dose limiting toxicity is encountered when the concentration of drug exceeds a specific threshold concentration and or duration at above a specific threshold concentration. Drugs do not have their intended effects once the level falls below the minimum effective plasma concentration.

Measurement of drug levels in blood is a useful tool but is only a surrogate for actual target tissue concentrations. Efficacy is correlated to the targeted duration and intensity of effect of drug, which depends on the rate of absorption, distribution and elimination (biotransformation, excretion). Standard oral, intravenous or intraperitoneal routes of administration suffer from a lack of targeting and relatively short duration of therapeutic drug level due to these effects, which often leads to under treatment of target tissue, off target and dose limiting toxicity and can result in selection bias towards chemoresistant disease (e.g. chemoresistant population of cells and cancer stem cells, etc.). Localized drug delivery at the site of disease has been long sought as a way to safely increase duration of therapeutic drug levels, reduce off-target systemic toxicity, eliminate chemoresistant selection bias by sustaining selective pressure. Therapeutic index is a comparison of the amount of a therapeutic agent that causes the therapeutic effect to the amount that causes toxicity. Producing a drug delivery technology which beneficially affects therapeutic index and delivers the drug only to where it is needed has historically been greatly desired but very challenging to achieve in practice.

Many of the pharmacological properties of conventional ("free") drugs can be improved through the use of drug delivery systems providing sustained release of biological and chemotherapeutic agents. Methods of regulated, slow, and localized drug release have considerable pharmacodynamic advantages for increasing the drug's efficacy and safety. Drug-resistant cancer cells that remain alive after chemotherapy are responsible for the reappearance of tumors and the poor prognosis for patients. Tumor resistance to chemotherapy in the clinic can be due to the inefficient distribution or short duration of therapeutic concentrations of drug relative to its targeted tumor tissue. The occurrence of drug resistance leads to the failure of tumor treatment. Drug resistance may be considered to be either intrinsic or acquired. Intrinsic resistance occurs when tumor cells are capable of escaping exposure or repairing damage induced by the cytotoxic effects of chemotherapy at initial exposure. Acquired resistance dominates when resistant cells survive from a population that was initially sensitive to chemotherapy. Drug delivery can be advanced by controlling the sustained diffusion of drugs to tumors through polymeric matrices and/or the degradation of these systems.

Sustained, therapeutic concentrations of drug released to targeted tumor enables superior patient compliance and patient outcomes, increases the therapeutic index of drugs and preventing the selection of chemoresistant cell populations. Sustained drug release is usually achieved either by incorporation of a therapeutic drug into an implantable reservoir or by implantation of biodegradable or non-biodegradable materials containing the desired drug. The drug can be actively expelled at a defined rate with a pump. Alternatively, drug can be released in a predictable and controlled manner passively from the implant by diffusion, erosion, or a combination of the two.

The development of biodegradable chemotherapeutic drug delivery implants is useful for the treatment of localized disease (e.g., malignancy or antimicrobial compounds for treating postsurgical infections or focal infections in immuno-compromised patients, etc.) Efficacies of slow drug release systems are usually determined by measurement of concentrations of the implanted drug in plasma or by assessment of the underlying disease treated (e.g., improving infection or decrease in the size of cancer, prevention of recurrence, etc.). For example, cancer chemotherapy delivery implants placed on a surgical margin would reduce the risk of localized recurrence. One example deals with the removal and/or resection of the chest wall in patients with sarcoma. The chest wall is the bone-and-tissue framework—including the spine, sternum, and ribs—that forms a cage around vital organs such as the heart and lungs. Many types of tumors can grow in this structure. Some are primary tumors, which originate in the chest wall and can be either benign or malignant; some are secondary tumors, which metastasize to the chest wall from another site in the body and are almost always malignant.

Malignant chest wall tumors include many types of sarcoma, which is a category of cancerous tumor that can form in bones, soft tissues, and cartilage anywhere in the body. Symptoms of chest wall sarcomas vary with the tumor's classification and severity, and could include difficulty breathing as well as pain and swelling surrounding the tumor.

Treatment can vary based on factors such as the type of tumor and the stage of its progression. Surgical resection is the mainstay of treatment for most early-stage chest wall tumors. Additional treatment can include radiotherapy (the use of radiation to kill cancer cells) and/or chemotherapy (the use of drugs to kill cancer cells). Local and distant recurrence is common. Localized drug delivery has proven a promising approach to prevent sarcoma recurrence in small animal models of disease. No effective treatment has yet been approved for use in humans which prevents recurrence.

Lung cancer is the largest cancer killer worldwide. The majority of lung cancers are discovered at late stage of the disease and are treated systemically. However, a significant portion of lung cancer patients are diagnosed at stage which can be treated with curative intent by surgery. In the case of operable lung cancer, when a patient is deemed physiologically healthy enough to tolerate surgery, surgical resection is the treatment of choice and offers the best chance for a cure. The operation for treating lung cancer can include: pneumonectomy, lobectomy (i.e., anatomic segmental resections along with their vascular supply and lymphatic drainage), segmentectomy or wedge resection. Instead of a pneumonectomy or lobectomy procedure, the physician may choose to perform a lesser resection in order to spare the loss of lung capacity and retain as much lung function postoperatively as possible but may compromise oncologic outcome due to the incomplete removal of tumor cells remaining in the lung resection margin. Wedge re-sectioning, or sublobar anatomic resection, involves the removal of a sublobar section of tissue mass encompassing the tumor or lesion including some margin beyond the original tumor. The resected tissue is secured with suturing or via a surgical staples. The staple line along the edges of the resection margin prevents air and blood leaks. In general, repair of the wedge resection is by way of the staple/resection line allowing the underlying organ to retain its shape without distortion. Typically, a wedge resection leaves just a single stitch line or staple line along the irregular resection edge. Despite the advantages concerning the surgical procedure, wedge resections have not been considered an optimal oncological resection method for cancer in patients who are fit physiologically to undergo lobectomies. What makes a wedge resection a compromise between retaining lung function and removal of all possible malignant tissue along the surgical margins is the observation that there is a higher rate of localized recurrence of cancer at the resection margin compared with lobectomy.

One method of localized treatment of resection margins used to prevent recurrence is brachytherapy. Brachytherapy involves application of a vicryl patch/mesh, into which brachytherapy seeds are sewn. The biodegradable mesh with radioactive seeds is then affixed to the lung tissue covering the resected area. Such a brachytherapy mesh is introduced though thoracotomy or minimally invasively through intercostal access with video assisted thorascopic surgery (VATS) and attached covering a resection staple line. A study found that the wedge and brachytherapy resulted in 1% local recurrence (LR), while wedge alone resulted in a 19% LR (see d'Amato et al., "Intraoperative Brachytherapy Following Thoracoscopic Wedge Resection of Stage 1 Lung Cancer", Chest Off. Pub. Of the Am. Coll. Of Chest Phys., 114(4):1112-5 October 1998). Adjuvant intraoperative brachytherapy does not appear to affect local recurrence when an anatomical segmentectomy with adequate surgical margins is performed. However, in high-risk patients not fit for anatomical resection, there may be a role for brachytherapy in reducing local recurrence when a sublobar non-anatomical resection is performed and in cases where the surgical margins are compromised. See e.g., Fernando H C, Landreneau R J, Mandrekar S J, Nichols F C, Hillman S L, Heron D E et al. Impact of brachytherapy on local recurrence rates after sublobar resection: results from ACOSOG z4032 (Alliance), a phase III randomized trial for high-risk operable non-small-cell lung cancer. J Clin Oncol 2014; 32: 2456-62]. Despite this limited positive result, the procedure has many practical disadvantages. First, it is operator dependent, thereby having variable results depending upon the experience of the surgical team. Second, reproducibility is tedious, especially in video-assisted cases adding an hour or more to the already complicated procedure in physiologically compromised patients. Third, the surgical and medical staff are exposed to unnecessary radiation during the surgical preparation and procedure. Despite the decrease in local recurrence, the above disadvantages, and others, have unfortunately prevented the widespread adoption of brachytherapy.

In many surgical procedures, including those involved in open, laparoscopic and endoscopic surgery, it is often necessary to fasten, staple, suture, glue, clip or clamp tissue together. Clinicians have been clamoring for surgical compositions and methods of using such compositions which can deliver drug locally to prevent recurrence or treat disease locally that are less operator dependent, reproducible, effective, and safe to both the patient and to those involved in the surgical procedure. Compositions and methods accomplishing such results include those described herein.

SUMMARY OF THE INVENTION

Presented herein are implantable compositions comprising a matrix together with at least one polymer and a therapeutically active agent.

Also presented herein is the use of these implantable compositions for the delivery (e.g., local delivery) of a therapeutically active agent to treat, ameliorate, or prevent the recurrence of a disease. Such diseases include e.g., those described herein.

Further presented herein is the use of these implantable compositions for inducing a disease state in a model system.

Among other properties described herein, the disclosed compositions are useful e.g., in overcoming problems associated with cancer recurrence due to, in one aspect, incomplete treatment of microscopic tumors. For example, surgical removal of tumors is typically the best treatment option for cure of certain cancers (such as lung cancer). In order to prevent recurrence, removal of an additional 10-20 mm resection margin is usually required. Because of old age, site of tumor, and multiple comorbidities, patients, however, generally cannot tolerate optimal resection. This leaves residual cancer cells and leads to recurrence. See e.g., FIG. 1. Placement of the implantable compositions described herein at the resection margin not only secures the integrity of the staple line (thereby preventing air and blood flow leaks), but also delivers sustained therapeutic concentrations of drug at highest risk of recurrence, effectively killing residual cancer cells and preventing recurrence. See e.g., FIG. 1.

Technical advantages and safety benefits associated with the compositions and uses thereof are described herein. Technical advantages include increased drug therapeutic index e.g., sustained therapeutic concentrations of drug to areas at highest risk of recurrence, low systemic release, no adverse effects on post-surgery healing (e.g., in the case of implantation on or at site of a surgical margin or lesion), compliance and non-eroding, high-toleration, easy to use in the standard of care surgery, and easily adaptable to embrace a vast range of therapeutic agents and procedures. See e.g., FIG. 2A-C.

BRIEF DESCRIPTION OF THE DRAWINGS

FIG. 2A-C illustrate that an exemplary composition described herein is effective and well-tolerated in tissue where FIG. 2A depicts the implantable composition on lung tissue together with a >25 mm penetration amount of the anti-cancer agent paclitaxel; FIG. 2B illustrates the percentage of paclitaxel (nM) vs. the penetration of paclitaxel (mm); and FIG. 2C illustrates the therapeutic concentration to be >30 nM.

FIG. 3 illustrates the repeatability of an application method for forming the compositions described herein.

FIG. 4A represents cumulative active agent release in ug/cm$^2$ vs. time; FIG. 4B represents cumulative active agent release in % vs. time; and FIG. 4C represents cumulative active agent release in ug vs. time.

FIG. 5A represents cumulative active agent release in ug/cm$^2$ vs. time; FIG. 5B represents cumulative active agent release in % vs. time; and FIG. 5C represents cumulative active agent release in ug vs. time.

FIG. 6A represents cumulative active agent release in ug/cm$^2$ vs. time; FIG. 6B represents cumulative active agent release in % vs. time; and FIG. 6C represents cumulative active agent release in ug vs. time.

FIG. 7A represents cumulative active agent release in ug/cm$^2$ vs. time; FIG. 7B represents cumulative active agent release in % vs. time; and FIG. 7C represents cumulative active agent release in ug vs. time.

FIG. 8A-C illustrate paclitaxel release between EtO (left) and non-EtO (right) treated compositions in units of ug/cm$^2$, %, and ug release using ABC103-A according to the present disclosure, where FIG. 8A represents cumulative active agent release in ug/cm$^2$ vs. time; FIG. 8B represents cumulative active agent release in % vs. time; and FIG. 8C represents cumulative active agent release in ug vs. time.

FIG. 13A-D illustrate a general schematic of a resection procedure using the compositions described herein, where FIG. 13A shows the tissue claimed between two stapler jaws; FIG. 13B shows staples are deployed; FIG. 13C show the remaining lung tissue; and FIG. 13D shows resected tissue.

FIG. 14A-C represent the microscopy of fixed stained tissues after treatment with an exemplified composition: FIG. 14A represents a control with uncoated buttress; FIG. 14B represents another control comprising buttress and no drug; and FIG. 14C represents an exemplified compositions.

DETAILED DESCRIPTION

A. Compositions

Figure 1:
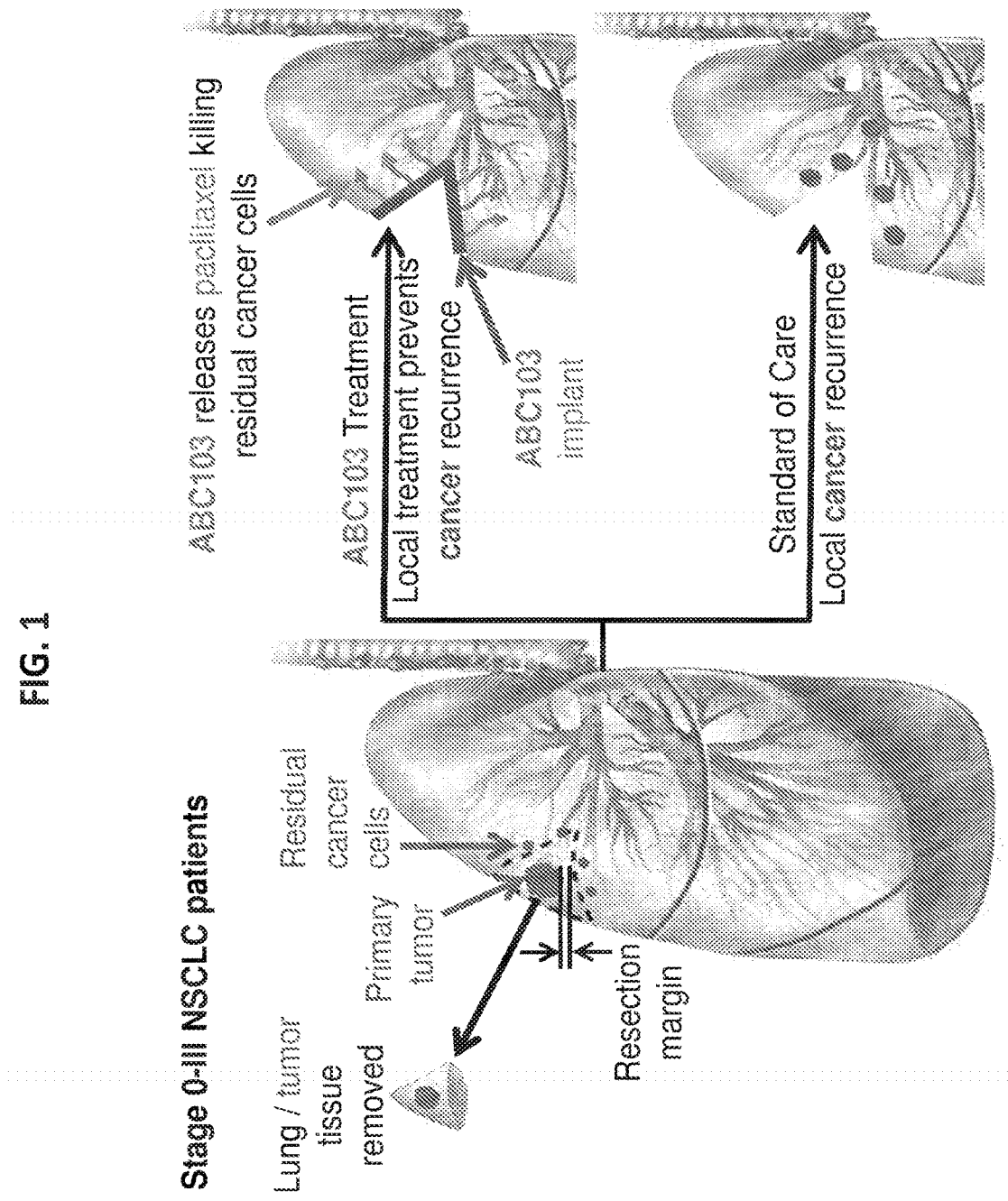
FIG. 1 depicts a problem with cancer recurrence and a solution provided by the compositions described herein.

In a first embodiment, the present disclosure provides an implantable composition comprising a matrix together with at least one polymer and a therapeutically active agent.

As will be understood, the term "implantable" refers to one or more layers of disclosed composition having mechanical properties sufficient to cover and/or be affixed to internal body tissue (e.g., to an internal surgical margin lesion). The term "implantable" may be used interchangeably with "implant." Examples of an implant include, but are not limited to, a surgical buttress or a surgical mesh comprising one or more of the features defined herein.

As used herein, ABC103-A comprises a PGA (Polyglycolic Acid) buttress material (Neoveil® or a suitable equivalent); ABC103-B comprises a PGA/TMC (Polyglycolic Acid/Trimethylene Carbonate) based buttress (e.g., GORE® SEAMGUARD®); and ABC103-C comprises a PGA buttress material (e.g., Neoveil®). Each of these formulations are comprised of a 25% PEG8K+50/50PLGA+Paclitaxel (if drug-loaded) coating on the given buttress material.

In a second embodiment, the present disclosure provides an implantable composition comprising a matrix together with at least one polymer, at least one excipient, and a therapeutically active agent.

In a third embodiment, the at least one polymer, at least one excipient, and therapeutically active agent in the first or second embodiment are separate and distinct entities.

In a fourth embodiment, the at least one polymer, at least one excipient, and therapeutically active agent of the first, second, or third embodiment are embedded in the matrix, coated on the matrix, embedded in and coated on the matrix, or covalently linked to the matrix. In an alternative, the at least one polymer, at least one excipient, and therapeutically active agent of the first, second, or third embodiment are embedded in and coated on the matrix.

In a fifth embodiment, the matrix of the compositions described herein comprises a membrane or porous scaffold, wherein the remaining features of the composition are as described herein e.g., as in the first, second, third, or fourth embodiment. Alternatively, the matrix of the compositions described herein comprises a membrane or non-porous scaffold, wherein the remaining features of the composition are as described herein e.g., as in the first, second, third, or fourth embodiment.

In a sixth embodiment, the matrix of the compositions described herein is a nonwoven or woven polymer mesh, wherein the remaining features of the composition are as described herein e.g., as in the first, second, third, fourth, or fifth embodiment.

In a seventh embodiment, the matrix of the compositions described herein is a biological matrix, wherein the remaining features of the composition are as described herein e.g., as in the first, second, third, fourth, fifth, or sixth embodiment. Biological matrices include e.g., any matrix derived from material or tissue in animal cells. Biologically based materials include e.g., hyaluronic acid, agarose, silk fobroin, self-assembling peptides, polysaccharidic materials, like chitosan, glycosaminoglycans, acellular dermal graft (ALLODERM), acellular collagen (PERISTRIPS) woven, knit or nonwoven and can be bioabsorbable or nonbioabsorbable. Biological matrices include those e.g., fabricated from homopolymers, copolymers or blends obtained from one or more monomers selected from the group consisting of glycolide, glycolic acid, lactide, lactic acid, p-dioxanone, α-caprolactone and trimethylene carbonate. Polymer matrices include, but are not limited to, poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends, and combinations thereof.

In an eighth embodiment, the matrix of the compositions described herein is a biological matrix selected from collagen sheets, bovine pericardium, human or animal dura or the like, wherein the remaining features of the composition are as described herein e.g., as in the first, second, third, fourth, fifth, sixth, or seventh embodiment.

In a ninth embodiment, the matrix of the compositions described herein is a polymer matrix comprising one or more of poly(ethylene) poly(propylene), poly(tetrafluroethylene), poly(methylmethacrylate), ethylene-co-vinylacetate, poly(dimethylsiloxane), poly(ether-urethanes), polycarbonate, polyethersulphone, polybenzimidazole, acrylonitrile butadiene styrene (ABS), polyvinyl chloride (PVC), polyether ether ketone (PEEK), poly(ethylene terphthalate), poly(sulphone), poly(esters) based on polylactide (PLA), polyglycolide (PGA), polycaprolactone (PCL), poly(hydroxyalkanoate)s, poly(saccharide)s, their copolymers and blends or combinations of copolymers and blends, wherein the remaining features of the composition are as described herein e.g., as in the first, second, third, fourth, fifth, or sixth embodiment. In an alternative, the matrix of the compositions described herein is a polymer matrix comprising polyglycolic acid (PGA), wherein the remaining features of the composition are as described herein e.g., as in the first, second, third, fourth, fifth, or sixth embodiment. In another alternative, the matrix of the compositions described herein is a biodegradable polyglycolic acid (PGA) mesh such as e.g., Neoveil® by Gunze and Bard Sepramesh by Covidien, wherein the remaining features of the composition are as described herein e.g., as in the first, second, third, fourth, fifth, or sixth embodiment. In yet another alternative, the matrix of the compositions described herein is a flexible composite mesh such as e.g., Parietex™ Composite (PCO) Mesh by Covidien, wherein the remaining features of the composition are as described herein e.g., as in the first, second, third, fourth, fifth, or sixth embodiment. In other alternatives, the matrix of the compositions described herein is a combination of polyglycolic acid and trimethylene carbonate, wherein the remaining features of the composition are as described herein e.g., as in the first, second, third, fourth, fifth, or sixth embodiment. In yet another alternative, the matrix of the compositions described herein is a polyglycolic acid:trimethylene carbonate (PGA:TMC) mesh having e.g., a PGA:TMC molar ratio of about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, or about 90:10, wherein the remaining features of the composition are as described herein e.g., as in the first, second, third, fourth, fifth, or sixth embodiment. In another alternative, the matrix of the compositions described herein is a polyglycolic acid:trimethylene carbonate (PGA:TMC) mesh having e.g., a PGA:TMC molar ratio of about 85:15 such as e.g., GORE® SEAMGUARD®, wherein the remaining features of the composition are as described herein e.g., as in the first, second, third, fourth, fifth, or sixth embodiment.

In a tenth embodiment, the therapeutically active agent of the compositions described herein comprises about 50% by weight or less of the total weight of the at least one polymer and at least one excipient embedded in the matrix, coated on the matrix, or embedded in and coated on the matrix, wherein the remaining features of the composition are as described herein e.g., as in the second, third, fourth, fifth, sixth, seventh, eighth, or ninth embodiment. Alternatively, the therapeutically active agent comprises about 25% by weight or less of the total weight of the at least one polymer and at least one excipient embedded in the matrix, coated on the matrix, or embedded in and coated on the matrix, wherein the remaining features of the composition are as described herein e.g., as in the second, third, fourth, fifth, sixth, seventh, eighth, or ninth embodiment. Alternatively, the therapeutically active agent comprises about 20% by weight or less of the total weight of the at least one polymer and at least one excipient embedded in the matrix, coated on the matrix, or embedded in and coated on the matrix, wherein the remaining features of the composition are as described herein e.g., as in the second, third, fourth, fifth, sixth, seventh, eighth, or ninth embodiment. In another alternative, the therapeutically active agent comprises about 15% by weight or less of the total weight of the at least one polymer and at least one excipient embedded in the matrix, coated on the matrix, or embedded in and coated on the matrix, wherein the remaining features of the composition are as described herein e.g., as in the second, third, fourth, fifth, sixth, seventh, eighth, or ninth embodiment. In yet another alternative, the therapeutically active agent comprises about 10% by weight of the total weight of the at least one polymer and at least one excipient embedded in the matrix, coated on the matrix, or embedded in and coated on the matrix, wherein the remaining features of the composition are as described herein e.g., as in the second, third, fourth, fifth, sixth, seventh, eighth, or ninth embodiment. In yet another alternative, the therapeutically active agent comprises about 5% by weight of the total weight of the at least one polymer and at least one excipient embedded in the matrix, coated on the matrix, or embedded in and coated on the matrix, wherein the remaining features of the composition are as described herein e.g., as in the second, third, fourth, fifth, sixth, seventh, eighth, or ninth embodiment. In yet another alternative, the therapeutically active agent comprises about 1% by weight of the total weight of the at least one polymer and at least one excipient embedded in the matrix, coated on the matrix, or embedded in and coated on the matrix, wherein the remaining features of the composition are as described herein e.g., as in the second, third, fourth, fifth, sixth, seventh, eighth, or ninth embodiment.

In an eleventh embodiment, the at least one excipient in the compositions described herein comprise about 50% by weight or less of the total weight of the at least one polymer and therapeutically active agent embedded in the matrix, coated on the matrix, or embedded in and coated on the matrix, wherein the remaining features of the composition are as described herein e.g., as in the second, third, fourth, fifth, sixth, seventh, eighth, ninth, or tenth embodiment. Alternatively, the excipient comprises between about 10% by weight to about 40% by weight of the total weight of the at least one polymer and therapeutically active agent embedded in the matrix, coated on the matrix, or embedded in and coated on the matrix, wherein the remaining features of the composition are as described herein e.g., as in the second, third, fourth, fifth, sixth, seventh, eighth, ninth, or tenth embodiment. In another alternative, the excipient comprises between about 5% by weight to about 50% by weight of the total weight of the at least one polymer and therapeutically active agent embedded in the matrix, coated on the matrix, or embedded in and coated on the matrix, wherein the remaining features of the composition are as described herein e.g., as in the second, third, fourth, fifth, sixth, seventh, eighth, ninth, or tenth embodiment. In another alternative, the excipient comprises between about 5% by weight to about 35% by weight of the total weight of the at least one polymer and therapeutically active agent embedded in the matrix, coated on the matrix, or embedded in and coated on the matrix, wherein the remaining features of the composition are as described herein e.g., as in the second, third, fourth, fifth, sixth, seventh, eighth, ninth, or tenth embodiment. In another alternative, the excipient comprises between about 5% by weight to about 20% by weight of the total weight of the at least one polymer and therapeutically active agent embedded in the matrix, coated on the matrix, or embedded in and coated on the matrix, wherein the remaining features of the composition are as described herein e.g., as in the second, third, fourth, fifth, sixth, seventh, eighth, ninth, or tenth embodiment.

As used herein, a "therapeutically active agent" refers to any agent that is capable of exerting a biological effect in vitro and/or in vivo that is therapeutic in nature.

In a twelfth embodiment, the therapeutically active agent of the compositions described herein is selected from synthetic organic molecules, proteins, enzymes, growth factors, polyanions, nucleosides, nucleotides, polynucleotides, and known pharmaceuticals and drugs containing the like, wherein the remaining features of the composition are as described herein e.g., as in the first, second, third, fourth, fifth, sixth, seventh, eighth, ninth, tenth, or eleventh embodiment. In one alternative, the therapeutically active agent of the compositions described herein is selected from (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromophone, and morphine; (3) salicylate analgesics, such as aspirin (ASA) (enteric coated ASA); (4) H1-blocker antihistamines, such as clemastine and terfenadine; (5) H2-blocker antihistamines, such as cimetidine, famotidine, nizadine, and ranitidine; (6) anti-infective agents, such as mupirocin; (7) anti-anaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous beta-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alpha, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fiuorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alpha, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) alpha-blocker sympatholytics, such as prazosin; (34) beta-blocker sympatholytics, such as atenolol; (35) adrenergic agonist sympathomimetics, such as albuterol and dobutamine; (36) cardiovascular agents, such as aspirin (ASA), plavix (Clopidogrel bisulfate) etc.; (37) beta-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I anti-arrhythmics, such as lidocaine, mexiletine, phenytoin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) alpha-blocker antihypertensives, such as prazosin; (46) angiotensin-converting enzyme inhibitor (ACE inhibitor) antihypertensives, such as captopril and enalapril; (47) beta blocker antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diurectic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents or enzymes, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical antiinfectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) immunosupressive agents, such as cyclosporin steroids, methotrexate tacrolimus, sirolimus, rapamycin; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic antianemia agents, such as erythropoietin, filgrastim (G-CSF), and sargramostim (GM-CSF); (78) coagulation agents, such as antihemophilic factors 1-10 (XHF 1-10); (79) anticoagulants, such as warfarin, heparin, and argatroban; (80) growth receptor inhibitors, such as erlotinib and gefetinib; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadatropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-Parkinson's agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) beta-blocker anti-glaucoma agents, such as timolol; (110) miotic anti-glaucoma agents, such as pilocarpine; (111) ophthalmic aminoglycoside antiinfectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; (129) vitamin D compounds, such as calcitriol; (130) vitamin A, vitamin E, and vitamin E compounds; (131) poisons, such as racin; (132) anti-bleeding agents, such as protamine; (133) antihelminth anti-infectives, such as metronidazole; and (134) sclerosants such as talc, alcohol, and doxycycline, wherein the remaining features of the composition are as described herein e.g., as in the first, second, third, fourth, fifth, sixth, seventh, eighth, ninth, tenth, or eleventh embodiment.

In a thirteenth embodiment, the therapeutically active agent of the compositions described herein is selected from anabolic agents, anesthetic agents, antacids, anti-asthmatic agents, anticholesterolemic and anti-lipid agents, anti-coagulants, anticonvulsants, anti-diarrheals, antiemetics, anti-infective agents, anti-inflammatory agents, anti-manic agents, anti-nauseants, antineoplastic agents, anti-obesity agents, anti-pyretic and analgesic agents, anti-spasmodic agents, anti-thrombotic agents, anti-uricemic agents, antianginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and prodrugs, wherein the remaining features of the composition are as described e.g., as in the second, third, fourth, fifth, sixth, seventh, eighth, ninth, tenth, or eleventh embodiment. Examples of specific drugs that can be used include: asparaginase, bleomycin, busulfan, capecitabine, carboplatin, carmustine, chlorambucil, cisplatin, cyclophosphamide, cytarabine, dacarbizine, dactinomycin, daunorubicin, dexrazoxane, docetaxel, doxorubicin, etoposide, fioxuridine, fludarabine, fluoruracil, gemcitabine, hydroxyurea, idarubicin, ifosfamide, irinotecan, lomustine, mechlorethamine, melphalan, mercaptupurine, methotrexate, mitomycin, mitotane, mitoxantrone, paclitaxel, pentostatin, plicamycin, premextred procarbazine, rituximabe, streptozocin, teniposid, thioguanine, thiotepa, vinplastine, vinchristine, and vinorelbine, wherein the remaining features of the composition are as described herein e.g., as in the first, second, third, fourth, fifth, sixth, seventh, eighth, ninth, tenth, or eleventh embodiment.

In a fourteenth embodiment, the therapeutically active agent of the compositions described herein is selected from an antifungal, an anti-infective antineoplastic, an anti-viral, an analgesic, a nonsteroidal anti-inflammatory drug, a narcotic, an alzheimer's agent, an anticancer agent an androgenic agent, an angiotensin modulator, an anticoagulant, a anticonvulsant, an antidepressant, an anti-Parkinson's agent, a antipsychotic, a antianginal, a beta and alpha blocker, a bone resorption suppression and related agent, a BPH agent, a bronchodialator anticholinergic and beta antagonist agent, a calcium channel blocker, a cytokine and CAM antagonist, a glucocorticoid, a hormone, a hepatitis treatment agent, a leukotriene modifier, a multiple sclerosis agent, a opthalmic glaucoma agent, and a pulmonary antihypertensive-endothelin receptor antagonist, wherein the remaining features of the composition are as described herein e.g., as in the first, second, third, fourth, fifth, sixth, seventh, eighth, ninth, tenth, or eleventh embodiment. In one alternative, the therapeutically active agent is an anticancer agent, wherein the remaining features of the composition are as described herein e.g., as in the first, second, third, fourth, fifth, sixth, seventh, eighth, ninth, tenth, or eleventh embodiment. In another alternative, the therapeutically active agent is an anticancer agent selected from an alkylating agent, a DNA crosslinking agent, an inhibitory nucleic acid, an anti-tumor antibiotic, a Tyrosine/Serine/Threnine kinase inhibitor, a topoisomerase inhibitor, a mitotic inhibitor, a corticosteroid, a therapeutic antibody, a biological response modifiers, or a microtubule stabilizer, wherein the remaining features of the composition are as described herein e.g., as in the first, second, third, fourth, fifth, sixth, seventh, eighth, ninth, tenth, or eleventh embodiment. In yet another alternative, the therapeutically active agent is selected from paclitaxel, discodermolide, epothilone A, epothilone B, epothilone C, epothilone D, epothilone E, epothilone F, epothilone B N-oxide, epothilone A N-oxide, 16-aza-epothilone B, 21-aminoepothilone B, 21-hydroxyepothilone D, prednisone, 26-fluoroepothilone, topotecan, bleomycin, doxorubicin, 5-fluorouracil, 6-mercaptopurine, capecitabine, cytarabine, floxuridine, fludarabine, gemcitabine, pemetrexed, actinomycin-D, irinotecan, etoposide, dexamethasone, FR-182877, BSF-223651, AC-7739, AC-7700, fijianolide B, laulimalide, caribaeoside, caribaeolin, taccalonolide, eleutherobin, sarcodictyin, laulimalide, dictyostatin-1, and jatrophane esters, and analogues and derivatives thereof, wherein the remaining features of the composition are as described herein e.g., as in the first, second, third, fourth, fifth, sixth, seventh, eighth, ninth, tenth, or eleventh embodiment.

In a fifteenth embodiment, the therapeutically active agent is paclitaxel or cisplatin, wherein the remaining features of the composition are as described herein e.g., as in the first, second, third, fourth, fifth, sixth, seventh, eighth, ninth, tenth, or thirteenth embodiment. Alternatively, the therapeutically active agent is paclitaxel, wherein the remaining features of the composition are as described herein e.g., as in the first, second, third, fourth, fifth, sixth, seventh, eighth, ninth, tenth, thirteenth, or fourteenth embodiment.

In a sixteenth embodiment, the therapeutically active agent is paclitaxel in an amount ranging from about 10 ug/cm$^2$ and about 450 ug/cm$^2$, wherein the remaining features of the composition are as described herein e.g., as in the first, second, third, fourth, fifth, sixth, seventh, eighth, ninth, tenth, fourteenth, or fifteenth embodiment. In one alternative, the therapeutically active agent is paclitaxel in an amount ranging from about 150 ug/cm$^2$ and about 300 ug/cm$^2$, wherein the remaining features of the composition are as described herein e.g., as in the first, second, third, fourth, fifth, sixth, seventh, eighth, ninth, tenth, fourteenth, or fifteenth embodiment. In another alternative, the therapeutically active agent is paclitaxel in an amount ranging from about 225 ug/cm$^2$ and about 275 ug/cm$^2$, wherein the remaining features of the composition are as described herein e.g., as in the first, second, third, fourth, fifth, sixth, seventh, eighth, ninth, tenth, fourteenth, or fifteenth embodiment. In another alternative, the therapeutically active agent is paclitaxel in an amount of about 250 ug/cm$^2$, wherein the remaining features of the composition are as described herein e.g., as in the first, second, third, fourth, fifth, sixth, seventh, eighth, ninth, tenth, fourteenth, or fifteenth embodiment.

In a seventeenth embodiment, the therapeutically active agent in the compositions described herein is encapsulated by a micro or nanostructure, wherein the remaining features of the composition are as described herein e.g., as in the first, second, third, fourth, fifth, sixth, seventh, eighth, ninth, tenth, eleventh, twelfth, thirteenth, fourteenth, fifteenth, or sixteenth embodiment.

In an eighteenth embodiment, the therapeutically active agent in the compositions described herein is encapsulated within a liposome, polymer, dendrimer, silicon or carbon material, or magnetic particle, wherein the remaining features of the composition are as described herein e.g., as in the first, second, third, fourth, fifth, sixth, seventh, eighth, ninth, tenth, eleventh, twelfth, thirteenth, fourteenth, fifteenth, sixteenth, or seventeenth embodiment.

In a nineteenth embodiment, the therapeutically active agent in the compositions described herein is encapsulated within a polymer, wherein the remaining features of the composition are as described herein e.g., as in the first, second, third, fourth, fifth, sixth, seventh, eighth, ninth, tenth, eleventh, twelfth, thirteenth, fourteenth, fifteenth, sixteenth, seventeenth, or eighteenth embodiment.

In a twentieth embodiment, the at least one excipient in the compositions described herein is selected from polyvinyl pyrrolidone (PVP), polyethylene oxide (PEO), polyvinyl alcohol (PVA), hydroxypropyl cellulose (HPC), hydroxypropylmethylcellulose acetate succinate (HPMCAS), ethylene vinyl acetate (EVA), methacrylates, ethyl cellulose (EC), cellulose acetate butyrate (CAB), cellulose acetate phthalate (CAP), polyethylene glycol, polyvinyl acetate (PVAc), polylactide (PLA), polyglycolide (PGA), copolymers of PLA/PGA and polycaprolactone (PCL), polyvinylpyrrolidone-co-vinyl acetate, and polyurethanes, wherein the remaining features of the composition are as described herein e.g., as in the second, third, fourth, fifth, sixth, seventh, eighth, ninth, tenth, eleventh, twelfth, thirteenth, fourteenth, fifteenth, sixteenth, seventeenth, eighteenth, or nineteenth embodiment. In one alternative, the at least one excipient is polyethylene glycol, wherein the remaining features of the composition are as described herein e.g., as in the second, third, fourth, fifth, sixth, seventh, eighth, ninth, tenth, eleventh, twelfth, thirteenth, fourteenth, fifteenth, sixteenth, seventeenth, eighteenth, or nineteenth embodiment.

In a twenty-first embodiment, the at least one excipient in the compositions described herein is polyethylene glycol having a molecular weight greater than about 1,000 g/mol, wherein the remaining features of the composition are as described herein e.g., as in the second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment. In one alternative, the at least one excipient is polyethylene glycol having a molecular weight ranging from about 2,000 g/mol to about 15,000 g/mol, wherein the remaining features of the composition are as described herein e.g., as in the second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment. In another alternative, the at least one excipient is polyethylene glycol having a molecular weight ranging from about 4,000 g/mol to about 10,000 g/mol, wherein the remaining features of the composition are as described herein e.g., as in the second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment. In another alternative, the at least one excipient is polyethylene glycol having a molecular weight ranging from about 7,000 g/mol to about 9,000 g/mol, wherein the remaining features of the composition are as described herein e.g., as in the second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment. In yet another alternative, the at least one excipient is polyethylene glycol 8000, wherein the remaining features of the composition are as described herein e.g., as in the second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment.

In a twenty-second embodiment, the at least one polymer in the compositions described herein is poly(lactic-co-glycolic acid) copolymer (PGLA), wherein the remaining features of the composition are as described herein e.g., as in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, or twenty-first embodiment.

In a twenty-third embodiment, the at least one polymer in the compositions described herein is poly(lactic-co-glycolic acid) copolymer (PGLA) having a lactide/glycolide molar ratio of about 20:80, about 25:75, about 40:60, about 45:55, about 53:47, about 55:45, about 50:50, about 60:40, about 75:25, or about 80:20, wherein the remaining features of the composition are as described herein e.g., as in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiment. Alternatively, the at least one polymer is poly(lactic-co-glycolic acid) copolymer (PGLA) having a lactide/glycolide molar ratio of about 50:50, about 47:53 and or about 53:47, wherein the remaining features of the composition are as described herein e.g., as in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiment. In another alternative, the at least one polymer is poly(lactic-co-glycolic acid) copolymer (PGLA) having a lactide/glycolide molar ratio of about 50:50, wherein the remaining features of the composition are as described herein e.g., as in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiment.

In a twenty-fourth embodiment, the at least one polymer in the compositions described herein is poly(lactic-co-glycolic acid) copolymer (PGLA) having a molecular weight ranging from about 20,000 g/mol to about 250,000 g/mol, about 50,000 g/mol to about 150,000 g/mol, about 65,000 g/mol to about 100,000 g/mol, about 70,000 g/mol to about 80,000 g/mol, or about 72,5000 g/mol, wherein the remaining features of the composition are as described herein e.g., as in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third embodiment.

B. Methods of Use

The compositions described herein, such as e.g., those exemplified in the first to twenty-fifth embodiments, are useful in treating or reducing the risk of acquiring a variety of diseases or conditions in a subject (e.g., a human) Such diseases and conditions are exemplified below.

As used herein, "reducing the risk of acquiring" is intended to mean to hinder, to stop, or to decrease the chance of getting a disease or condition described herein. The term "reducing the risk of acquiring" may be used interchangeably with "reduce the risk of acquiring" and "reduced the risk of acquiring." Reducing one or more of the conditions described herein can include e.g., avoiding or decreasing one or more risk factors associated with a given disease or disorder. In the case of a cancer e.g., avoiding or decreasing the risk of recurrence of that cancer, or other potential cancers, by affixing a composition as defined herein would be deemed as "reducing the risk of acquiring" of that cancer. For example, and in the case of affixing a composition described herein to a susceptible individual prior to the onset of symptoms or diagnosis (e.g., in light of a history of symptoms and/or in light of genetic or other susceptibility factors, including symptoms or conditions that are known or susceptible to arise from, or recur from, the surgical removal of the condition), i.e., prophylactic treatment.

As used herein, the terms "treatment," "treat," and "treating" refer to reversing, alleviating, further inhibiting the progress of, or inducing remission of a disease or disorder, or one or more symptoms thereof, as described herein after the condition or one or more symptoms have developed; i.e., therapeutic treatment. In one aspect, treatment is therapeutic.

Conditions or diseases include e.g., those described in and/or treatable by the therapeutically active agents defined in the compositions above e.g., as in the first to twenty-fifth embodiments. In one embodiment, the condition or disease treated by the compositions described herein, e.g., as in the first to twenty-fifth embodiments is cancer.

In one embodiment, the conditions or diseases treatable by the compositions defined herein, such as, e.g., those recited in the first to twenty-fifth embodiments, or a disease or condition to which the risk of acquiring is reduced by the aforementioned compositions, is a disease that may exhibit post-surgical local reoccurrence and, is some instances those diseases that also reoccur locally at the site of resection. Such diseases and conditions include e.g., head and neck cancer, chest cancer, eye cancer, nose cancer, throat cancer, lung cancer, breast cancer, anal cancer, abdominal cancer, and bladder cancer.

In one embodiment, the condition or disease treated by the compositions described herein is a lung cancer. Thus, in one embodiment, the present disclosure provides a method of treating or reducing the risk of acquiring a cancer (e.g., a lung cancer) in a subject comprising affixing in or on the subject, a composition described herein, e.g., as described in the first to twenty-fifth embodiments.

As described above, the compositions described herein may be affixed (e.g., surgically affixed) in or on the subject. In the case of a disease or disorder to which post-surgical local reoccurrence occurs and, in instances where reoccurrence occurs locally at the site of resection (such as e.g., in the case of resection following removal of a lung cancer), the compositions described herein may be affixed directly in or on the site of resection, surgical margin, or lesion. Compositions include e.g., those described in the first to twenty-fifth embodiments. Thus, in one aspect, the compositions described herein, e.g., those described in the first to twenty-fifth embodiments, can be affixed in or on e.g., the thorax of a subject in need thereof, in or on the abdomen of the subject, in or on an extremity of the subject, in or on the head of a subject in need thereof, in or on the neck of a subject in need thereof, in or on the pulmonary system of a subject in need thereof, in or on the eyes of a subject in need thereof, in or on the nose of a subject in need thereof, or in or on the throat of a subject in need thereof, or a combination thereof.

In one embodiment, a composition described herein, e.g., those in the first to twenty-fifth embodiments, is affixed in or on the lungs of a subject. In another embodiment, the aforementioned composition is affixed in or on the lung tissue of a subject in need thereof. For example, in another embodiment, the present disclosure provides a method of treating or reducing the risk of acquiring a lung cancer in a subject in need thereof comprising affixing in or on the lung tissue of the subject, a composition described herein, e.g., as described in the first to twenty-fifth embodiments. In yet another embodiment, the present disclosure provides a method of treating or reducing the risk of acquiring a lung cancer in a subject in need thereof comprising affixing at the site of a surgical margin or lesion resulting from the removal of a lung cancer in the subject, a composition described herein, e.g., as described in the first to twenty-fifth embodiments.

Figure 19A:
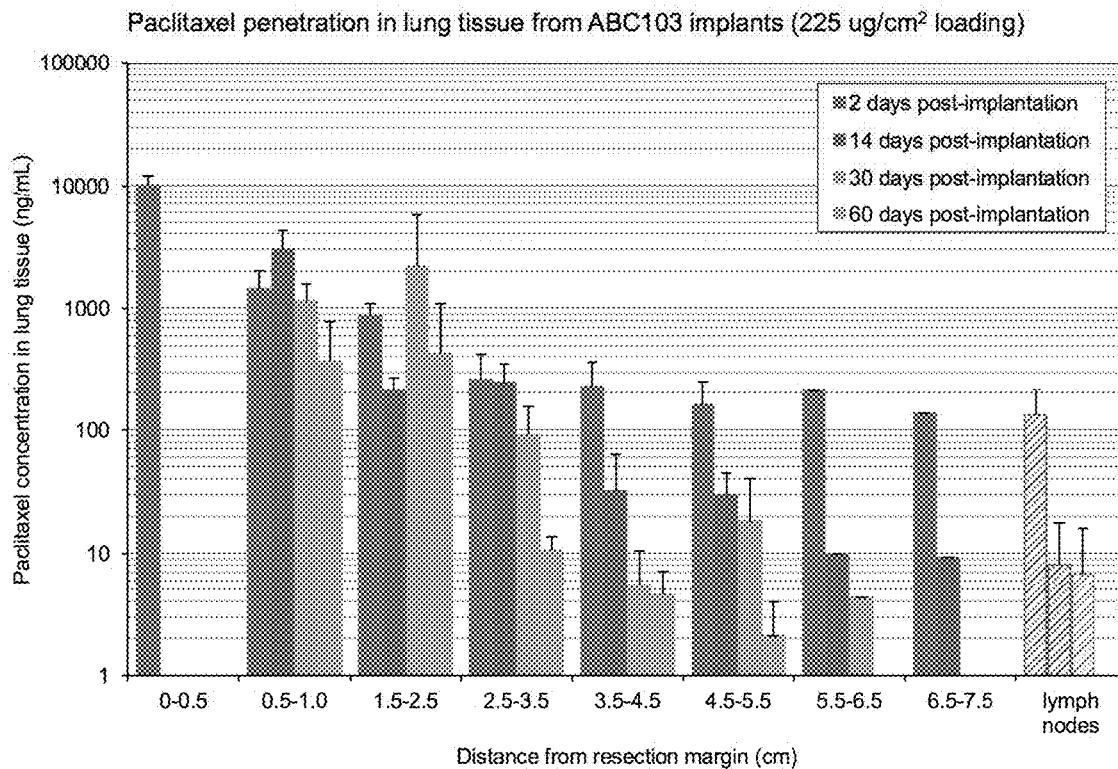
FIG. 19A-B illustrate the in vivo distribution of paclitaxel in FIG. 19A pig lungs and FIG. 19B organs at 2, 14, 30 and 60 days post implantation of ABC103-A implants at a dose of 225 ug/cm$^2$.
Figure 19B:
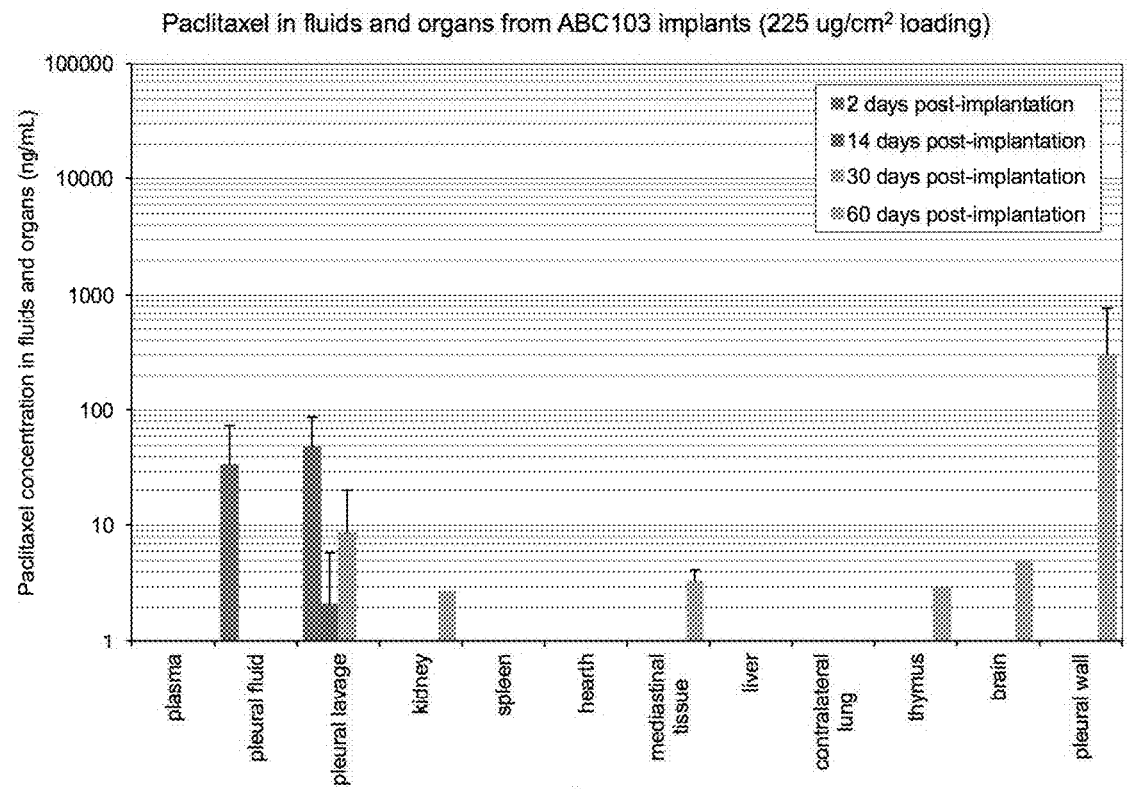

In one embodiment, the compositions described herein, e.g., those in the first to twenty-fifth embodiments, were found to deliver therapeutically active agent (e.g., paclitaxel) to mediastinal tissue, brain, thymus, and kidney. See FIG. 19A-B. Thus, provided herein are methods of delivering a therapeutically active agent to the lymphatic system using the compositions described herein e.g., those in the first to twenty-fifth embodiments.

In one embodiment, the compositions described herein, e.g., those in the first to twenty-fifth embodiments, exhibit continuous, variable, or sigmoidal release of the therapeutically active agent (e.g., paclitaxel).

In another embodiment, and/or in combination with the preceding embodiments, the compositions described herein, e.g., those in the first to twenty-fifth embodiments maintain continuous release of the therapeutically active agent (e.g., paclitaxel) at <about 100 nM, at <about 50 nM, at about 2 to about 20 nM. In one instance, continuous release is about 20 nM per day. In some instances, and/or in combination with the preceding embodiments, no toxic effects are exhibited at <about 100 nM of paclitaxel.

In one embodiment, and/or in combination with the preceding embodiments, the compositions described herein, e.g., those in the first to twenty-fifth embodiments maintain sustained release of paclitaxel at <about 100 nM per day, at <about 50 nM per day, at about 2 to about 20 nM per day. In one instance, sustained release is about 20 nM per day. In some instances, and/or in combination with the preceding embodiments, no toxic effects are exhibited at <about 100 nM per day of paclitaxel.

In one embodiment, and/or in combination with the preceding embodiments, greater than 70%, greater than 75%, greater than 80%, or greater than 85% of the therapeutic agent paclitaxel is released using the compositions described herein, e.g., those in the first to twenty-fifth embodiments.

In one embodiment, and/or in combination with the preceding embodiments, complete dissolution of the therapeutic agent paclitaxel is maintained throughout delivery and release.

C. Technical Advantages

The following represent certain technical advantages of the compositions disclosed herein. These advantages are in no way limiting and are provided for illustrative purposes only. They are not intended to, nor should they be construed to, limit the scope of the invention. In will further be understood that the advantages described herein are intended to in no way be comprehensive of all the advantages of the present compositions. Rather, the advantages described below merely represent certain technical features to further illustrate the problems solved by the instant invention.

As explained above, in many surgical procedures, including those involved in open and endoscopic surgery, it is often necessary to fasten, staple, suture, glue, clip or clamp tissue together. Surgical closure devices like stapling devices have found widespread application in surgical operations where body tissue must be joined or removed. When operating on thin tissue, such as thin emphysematous lung tissue, it is important to effectively seal the tissue which can be particularly prone to air leakage. Preventing or reducing air leakage can significantly decrease post-operative recovery time. Thus, it would be advantageous to provide a surgical mesh or surgical buttress that would effectively affix to and seal the surgical site at the site of resection. The compositions described herein produce such a result as shown e.g., in FIG. 1 where lung tissue remained sealed without leaks after a 14 day affixation with a composition according to the present disclosure. Further details are described e.g., in the Exemplification section below.

In addition to providing an adequate seal at the site of resection, another advantage would be to affix a composition that also comprises drug-eluting effects. This would be particularly important in cases following the removal of infected or malignant tissue. As explained above with respect to cancer for example, wedge resection is undesirable because of a 19% rate of localized recurrence of cancer at the resection margin. The compositions described herein, however, are not only effective in sealing the site of resection, but also locally deliver therapeutic concentrations of drug to the affixed site (tissue). Thus, e.g., following the removal of one or more malignancies (such as e.g., from the lungs of a patient), the present compositions can be affixed to seal the surgical margin (or be affixed to a lesion) and effectively seal the site and deliver therapeutic concentrations of active agents (e.g., anticancer agents such as paclitaxel and/or cisplatin) to prevent local reoccurrence.

In addition to sealing the site of resection to increase healing time and locally delivering therapeutic concentrations of drug to the affixed tissue, the present compositions further result in superior dosing properties. Therapeutic agents of the compositions described herein are not released systemically. See e.g., FIG. 14A-C. No adverse effects on post-healing were observed and the compositions were well tolerated in vivo as described in the exemplification section below. In the case of compositions comprising the therapeutic agent paclitaxel, no toxicity was observed even with release at >50 nM concentrations and regardless of the release trend, i.e., continuous, variable, sigmoidal, burst release, combinations thereof, etc. Also, complete dissolution (infinite sink) was maintained throughout delivery and release with the present compositions comprising the therapeutic agent paclitaxel. The dose delivery rate in these cases being between about 10.1 mg per patient for a composition comprising 450 ug/cm$^2$ and a 10% paclitaxel concentration.

Yet another advantage of the present compositions is the minimization of dose dumping and adverse effects due to drug degradation. In the case of paclitaxel, the present compositions locally deliver above 80% of this therapeutic agent to the target tissue while still producing a therapeutic effect. See e.g., FIGS. 4C to 8C, which show the actual cumulative concentration release of paclitaxel delivered per day. Because of this, and the advantages discussed above, less overall drug (i.e., paclitaxel) is needed and, therefore, decreases the risks associated with dose dumping (such as in into non-targeted areas) and is much safer to use since de minimis amounts remain for degradation.

These technical advantages cumulatively provide a single composition that can be used to effectively seal the site of resection following the removal of infected or malignant tissue and, in addition, locally treat the site of resection with a therapeutic agent, where the composition effectively delivers to a broad local area of tissue for at least a period of 60 day (or at least a period of 30 days), without any observable toxic effect. In other words, no adverse effects were seen at all during these periods.

Certain exemplary provided compositions and uses described above are set forth in the EXEMPLIFICATION section below. In some embodiments, a provided composition and/or use is one or more selected from those exemplified in the EXEMPLIFICATION section below.

EXEMPLIFICATION

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples that follow and the references to the scientific and patent literature cited herein. It should further be appreciated that the contents of those cited references are incorporated herein by reference to help illustrate the state of the art.

Therapeutic levels of paclitaxel were delivered to >2.5 cm of lung tissue at 14 days with both 1%, 5% and 10% paclitaxel coated buttress implants. The procedure and implants were well tolerated. Normal healing was observed with all implants even with uM concentrations of drug immediately under the therapeutic implant. Paclitaxel levels were below 0.5 pg/ml in blood at 2, 7 and 14 days and measured in pleural fluid 10-100 nM.

For measurements, 1% is equal to or approximately 25 ug/cm$^2$, 5% is equal to or approximately 120 ug/cm$^2$, 10% is equal to or approximately 225 ug/cm$^2$, and 20% is equal to or approximately 415 ug/cm$^2$.

I. General Procedure and Methods of Development for In-Vitro Release

Figure 4A:
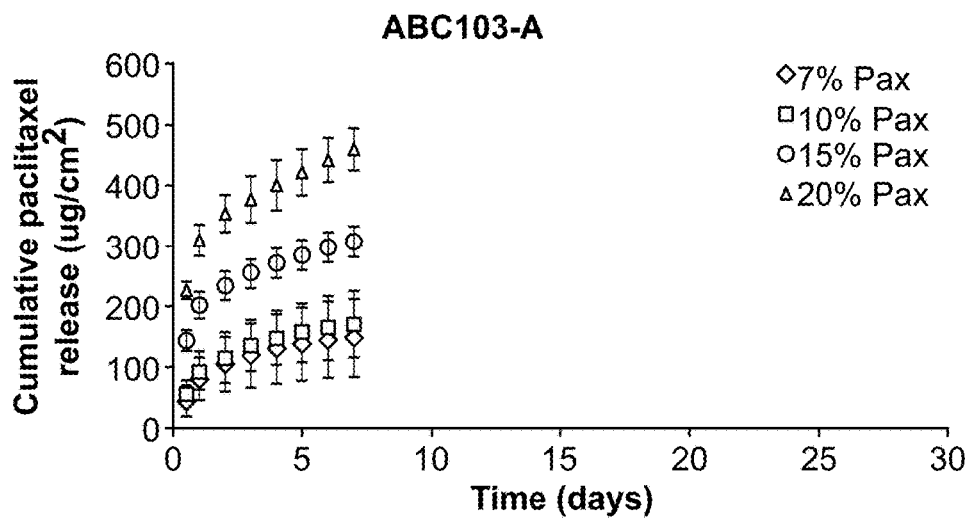
FIG. 4A-C illustrate in-vitro release data using ABC103-A according to the present disclosure with increasing therapeutically active agent loading, where
Figure 4B:
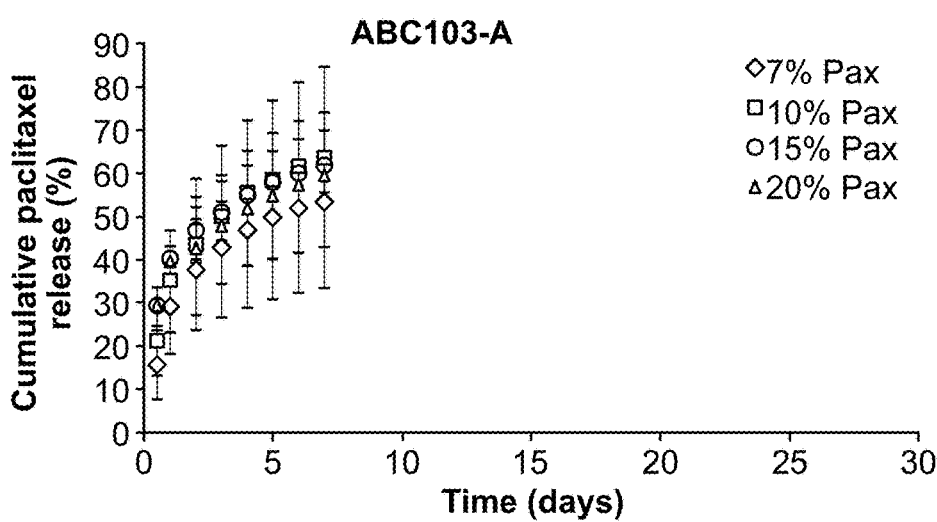
Figure 4C:
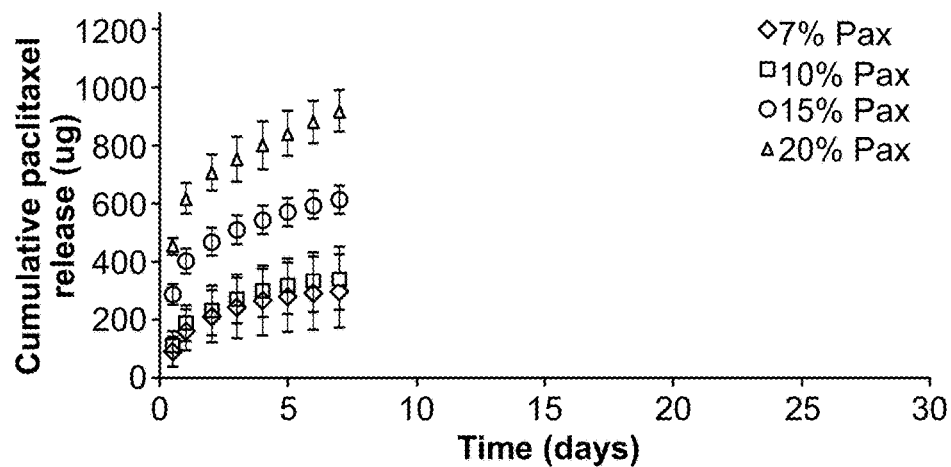
Figure 5A:
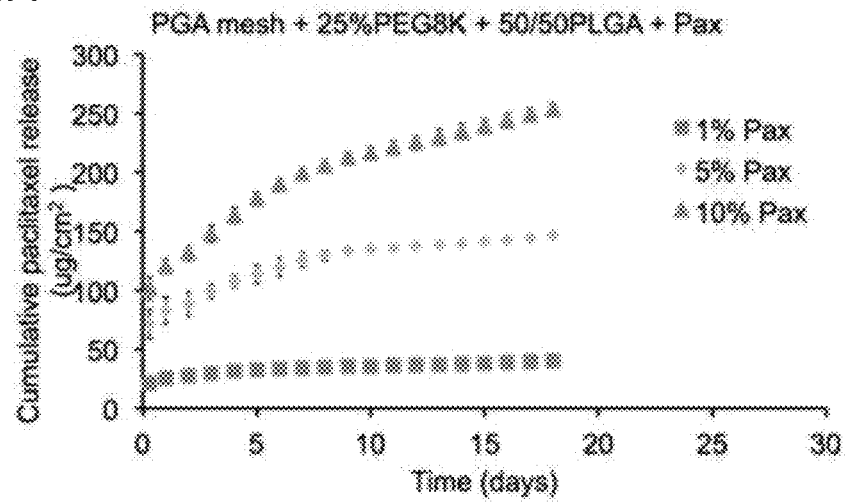
FIG. 5A-C illustrate in-vitro release data of a follow-up study using ABC103-A according to the present disclosure and 1%, 5%, and 10% therapeutically active agent loading, where
Figure 5B:
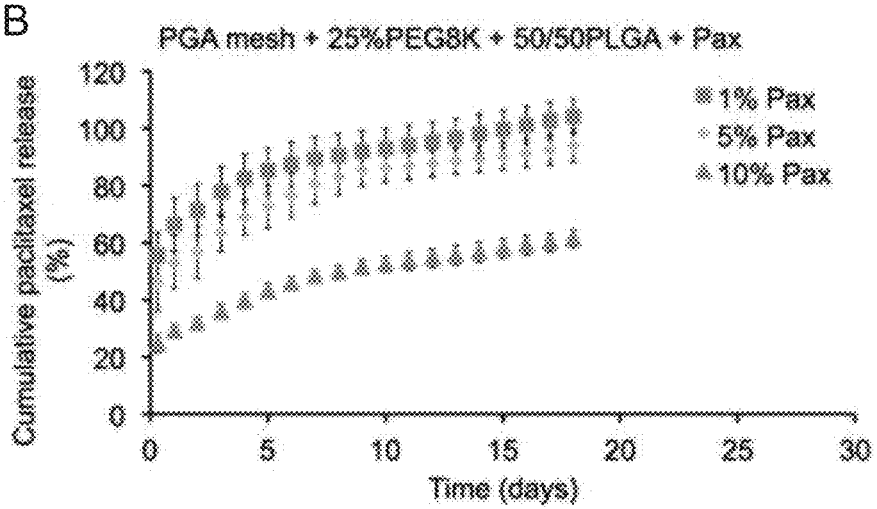
Figure 5C:
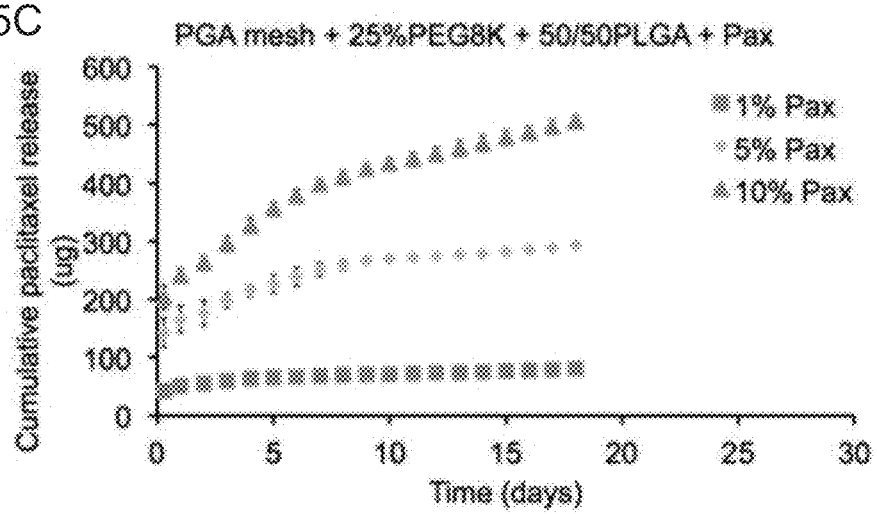

Using a film applicator/Gate method, a composition as described herein comprising 7%, 10%, 15%, and 20% Paclitaxel was prepared by coating a PGA or PGA/TMC mesh with 20% wt/vol. solutions of 25% PEG8K 50/50PLGA+Pax. FIG. 3 illustrates the repeatability between sample from different locations on the substrate. As shown by FIG. 4A-C, release data demonstrated increasing burst and overall release with increasing Paclitaxel (Pax) loading.

Figure 7A:
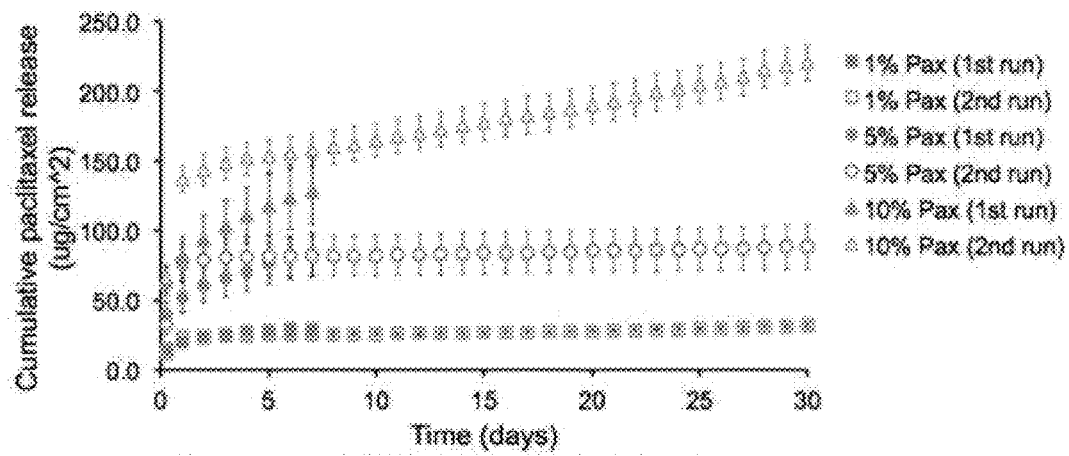
FIG. 7A-C illustrate in-vitro release data using ABC103-A according to the present disclosure with increasing therapeutically active agent loading, where
Figure 7B:
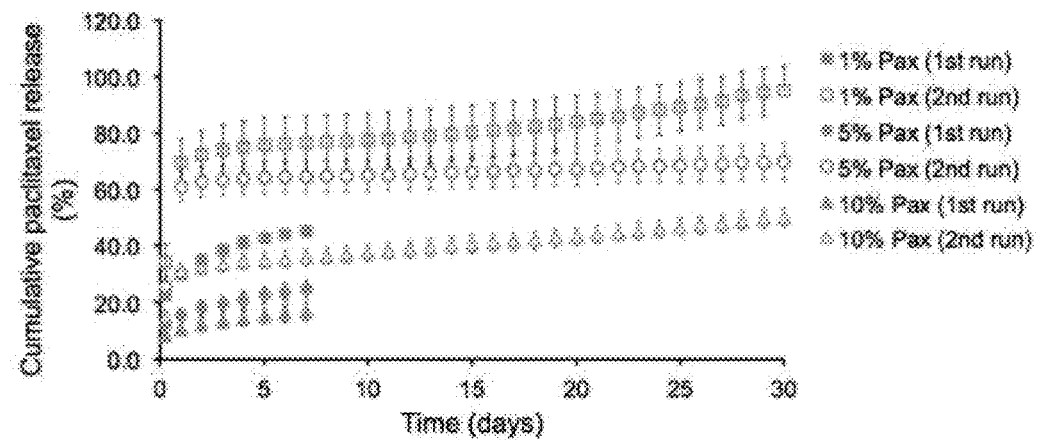
Figure 7C:
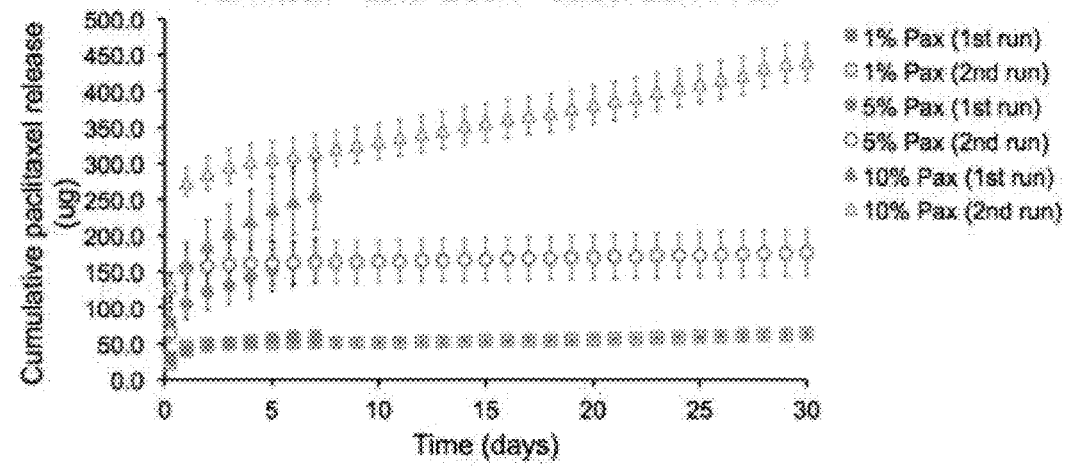

A followup study was conducted using 1%, 5%, and 10% Pax loaded formulations to reduce the amount of drug released (ug/day). See FIG. 5A-C. FIG. 7A-C show data from two additional release studies, one of which was carried out to 30 days.

Figure 6A:
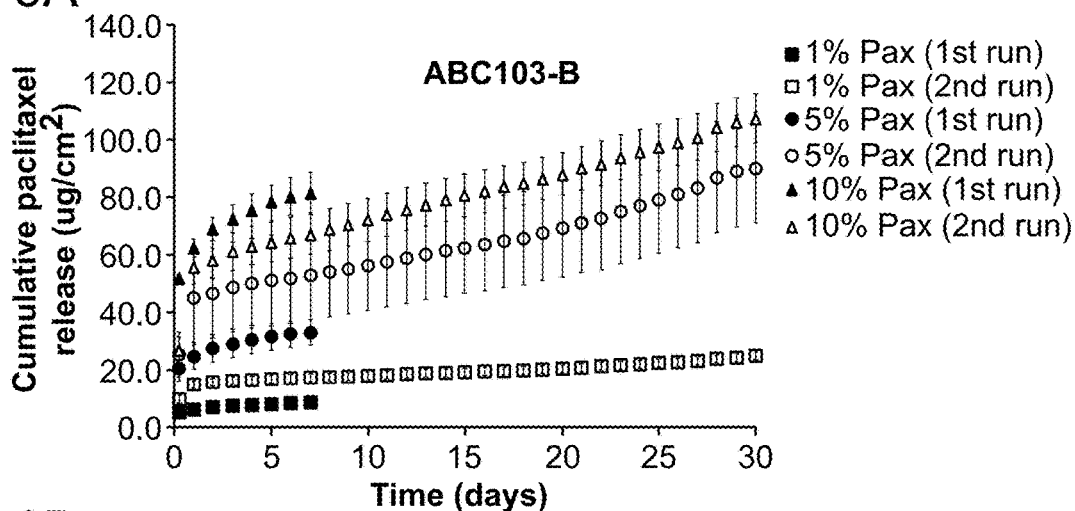
FIG. 6A-C illustrate in-vitro release data using ABC103-B according to the present disclosure with increasing therapeutically active agent loading, where
Figure 6B:
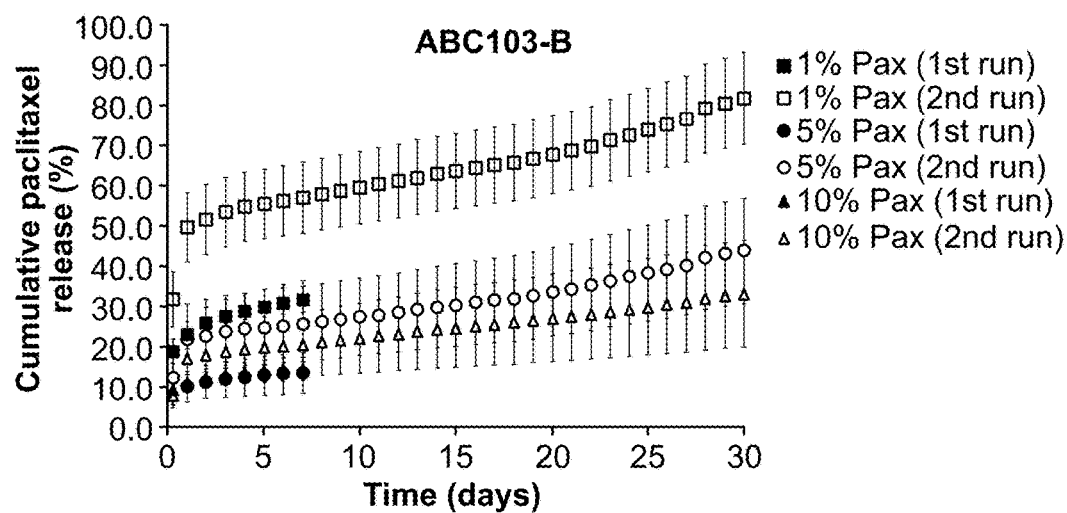
Figure 6C:
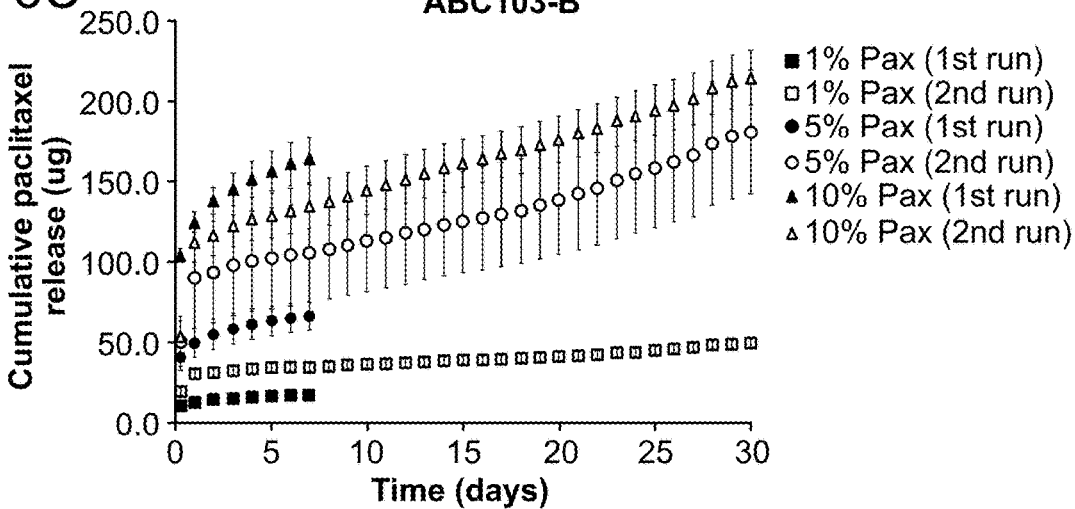

Similar experiments were performed using other buttress materials. For example, a PGA/TMC buttress (GORE® SEAMGUARD) was used as comparative commercial controls. The results of this experiments are shown in FIG. 6A-C.

2. In-Vitro+/−Sterilization Effects

Certain effects on the in vitro release of the disclosed compositions were seen upon treatment with Ethylene Oxide (EtO). For example FIG. 8A-C show that EtO treatment inhibits paclitaxel (Pax) release by all metrics (ug, %, ug/cm^2) in all formulations. This affect appeared most pronounced at the highest % Pax formulas. Surprisingly, however, even though this result would appear to have an adverse effect on increased amount of drug loading, it did not appear to have a pronounced effect in vivo. Indeed, the slowing of the paclitaxel release (and the decrease in burst release at high % Pax loadings) may be another cumulative effect as to why the disclosed compositions perform exceptionally in vivo.

3. General Procedure for Rabbit Lung Implant Study Using the Present Compositions An incision at the 8$^{th}$ intercostal space was made into the thorax of anesthetized rabbits. The Caudal lobe was partially released from the underlying ligament. Implants were affixed as a sandwich at the apical end of a resected caudal lobe. In all cases, 2 implants top & bottom were preloaded onto a 30 mm GIA stapler. Stapling and resection were performed using a 30 mm GIA stapler. Animals were sutured, air was removed from the thorax and the wound covered. All animals tolerated the procedure and recovered normally. A general schematic of the reset procedure is provided by FIG. 13A-D. For example, the stapler jaws (with the implant) are positioned to grasp the tissue (FIG. 13A). Staples are then deployed through the implant securing it to the tissue at the same time as the internal blade bisects the stapled tissue (FIG. 13B). The now bisected implant is released from the stapler. The resected tissue is removed. The implants are held with staples to the resection margin preventing air and blood leaks and locally administering paclitaxel (FIG. 13C).

a. Compositions Tested

Standard PGA buttress (i.e., PGA mesh).

Standard PGA buttress (i.e., PGA mesh)+PLGA/PEG coating—unloaded ABC103-A

Standard PGA buttress (i.e., PGA mesh)+PLGA/PEG coating with 1% w/w of drug (Paclitaxel) in coating—ABC103-A 25 ug/cm$^2$.

Standard PGA buttress (i.e., PGA mesh)+PLGA/PEG coating with 5% w/w of drug (Paclitaxel) in coating—ABC103-A 120 ug/cm$^2$.

Standard PGA buttress (i.e., PGA mesh)+PLGA/PEG coating with 10% w/w of drug (Paclitaxel) in coating—ABC103-A 225 ug/cm$^2$.

PGA/TMC buttress (GORE® SEAMGUARD).

PGA/TMC buttress (GORE® SEAMGUARD)+PLGA/PEG coating—unloaded-ABC103-B.

PGA/TMC buttress (GORE® SEAMGUARD)+PLGA/PEG coating with 1% w/w of drug (Paclitaxel) in coating—ABC103-B 25 ug/cm$^2$.

Each sample type was tested in two animals. Basis weight of coated buttress increased about 50% compared to uncoated buttresses.

b. Paclitaxel Analysis and Histology

Figure 9:
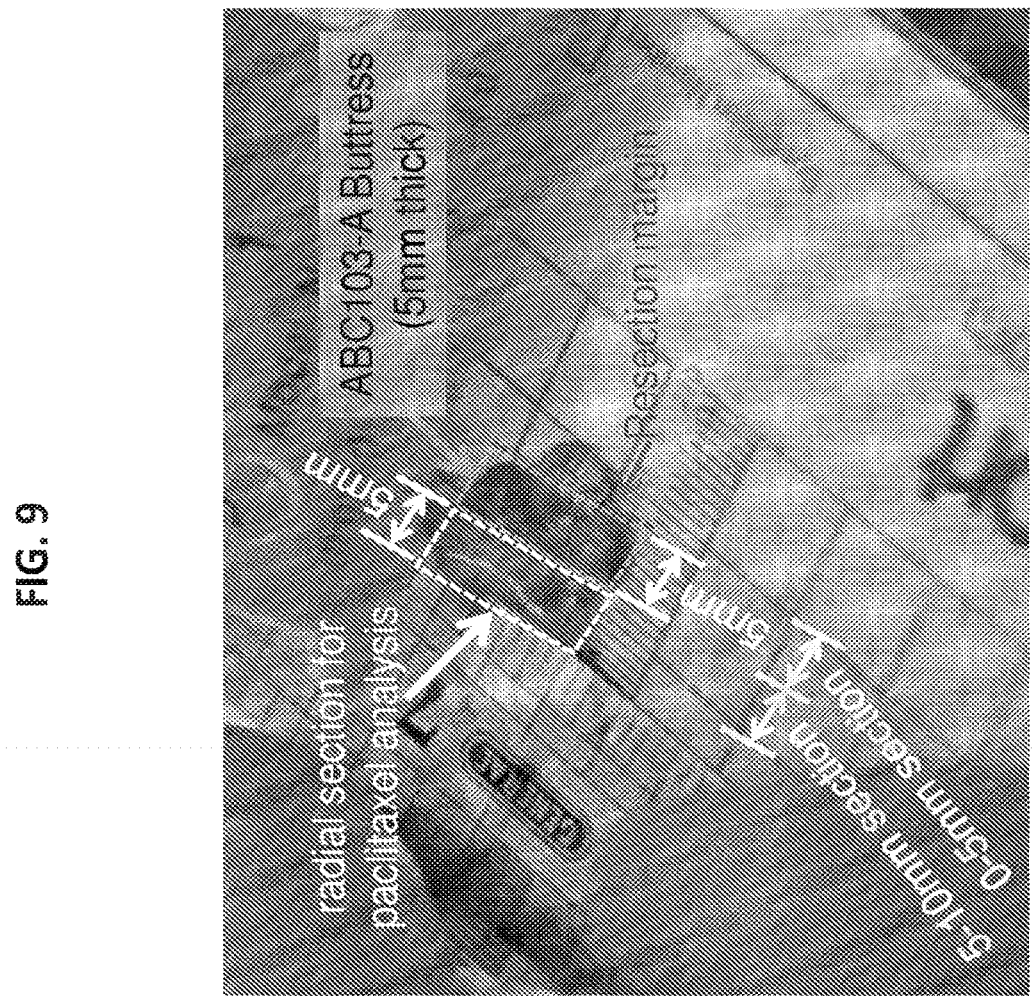
FIG. 9 illustrates a section of lung for paclitaxel analysis.

Blood, pleural fluid and tissue were assayed for paclitaxel concentrations. Paclitaxel concentrations in blood were taken at 2 days, 7 days and terminally at 14 days and determined to be below quantifiable limits (<500 pg/ml). No paclitaxel metabolites were measured as part of this protocol. Paclitaxel in pleural fluid was tested on day 0 and day 14 at necropsy, and lung tissue on day 14 at necropsy. All major organs and chest wall at the incision were recovered and divided in two with one half frozen −80° C. for later paclitaxel analysis and the other half fixed in formalin for later histology. FIG. 9 illustrates recovery method for serial 5 mm sections of lung for paclitaxel analysis out to 2.5 cm from cut edge. Table 1 below shows paclitaxel tissue concentrations in rabbit lung at 5 mm radial intervals away from the resection margin (nM).

TABLE 1

Paclitaxel Tissue Concentrations in Rabbit Lung at 5 mm Radial Intervals away from the Resection Margin (nM)

| mm | ABC103-A 25 ug/cm2 | ABC103-A 25 ug/cm2 | ABC103-A 225 ug/cm2 | ABC103-A 225 ug/cm2 |
| --- | --- | --- | --- | --- |
| 0-5 | 1100 | 792 | 3,020 | 14,200 |
| 5-10 | 98 | 34 | 372.5 | 41.6* |
| 10-15 | 54 | 20.9 | 283.2 | 293.8 |
| 15-20 | 47.9 | 12.6 | 361.9 | 484.1 |
| 20-25 | 15 | 9.58 | 357.2 | 136.3 |

Figure 10:
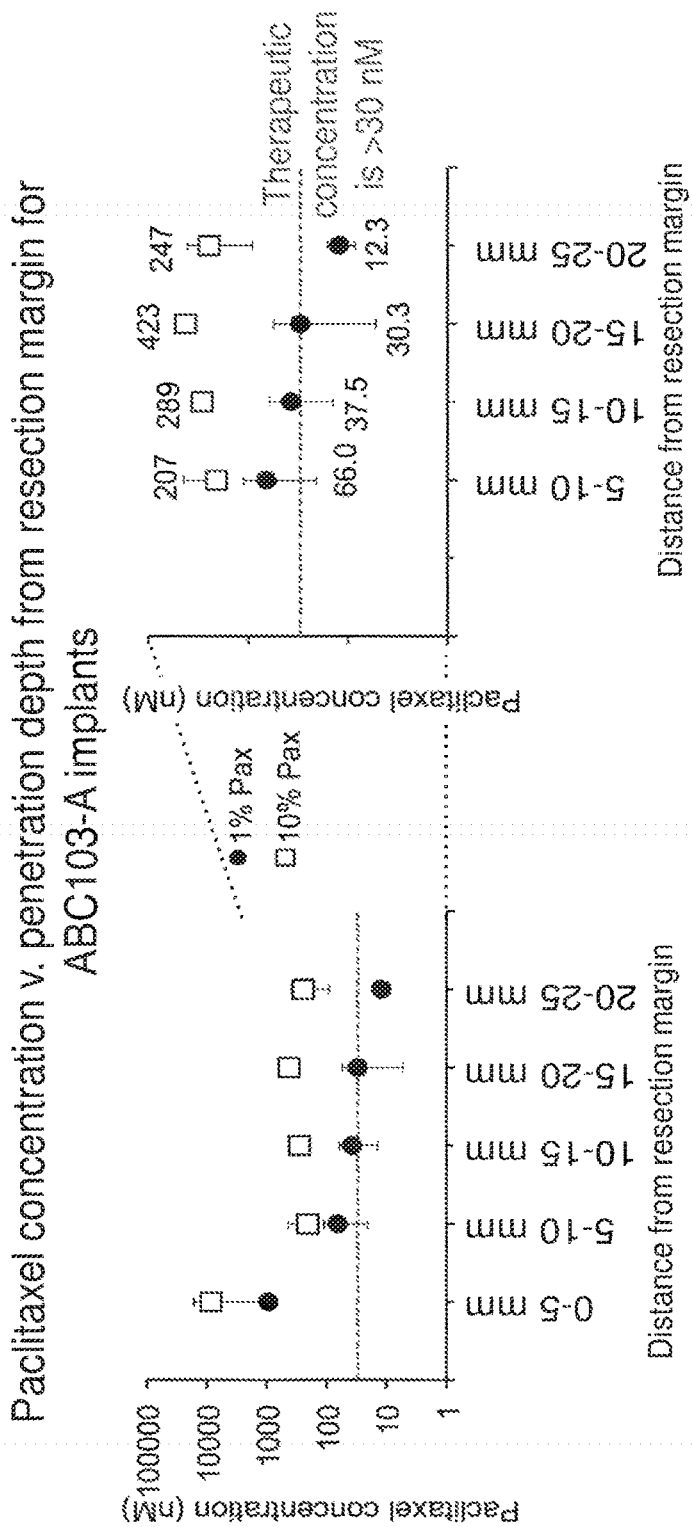
FIG. 10 illustrates paclitaxel drug per radial section of lung, for 1% paclitaxel and 10% paclitaxel loaded compositions of ABC103-B.

FIG. 10 illustrates paclitaxel drug in nanomolar concentration per 5 mm radial section of lung at 1% and 10%. The therapeutic concentration range for paclitaxel was found to be IC$_{50}$=>7 nM or about 6 ng/ml and IC$_{90}$=about 50 nM or about 42.5 ng/ml. The data point for concentration of paclitaxel directly under the implant was not included in the graphs for clarity 5 mm is at the resection edge under the implant. The data is uneven due to the low number of animals tested in this pilot experiment (n=2 rabbits).

Figure 11:
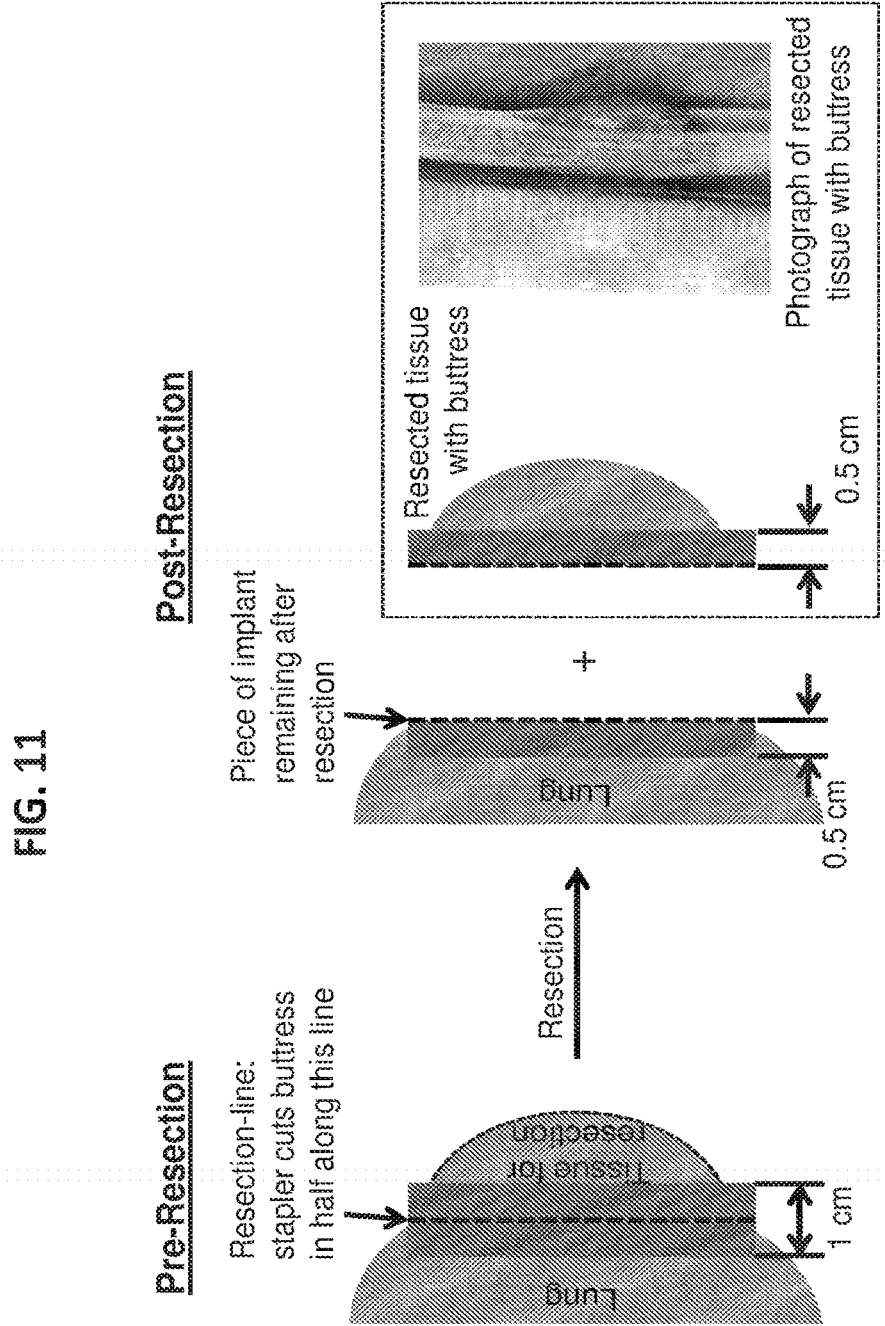
FIG. 11 is an example of resecting and removing one of the in vivo sections of an implantable composition described herein.

FIG. 11 is an example of resecting and removing half of the implantable compositions where in vivo sections were trimmed down to no more than 5 mm wider than the underlying lung.

Figure 12B:
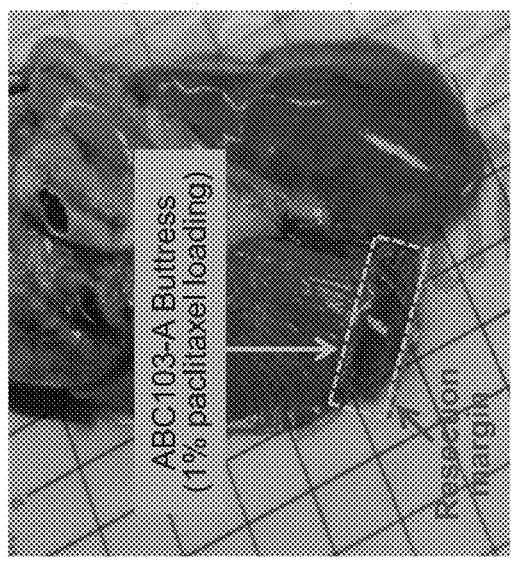
FIG. 12A-D illustrate rabbit lung tissue after 14 day affixation with a PGA based buttress composition having: no therapeutically active agent FIG. 12A, 1% of therapeutically active agent FIG. 12B, 5% of therapeutically active agent FIG. 12C and 10% of therapeutically active agent FIG. 12D.
Figure 12D:
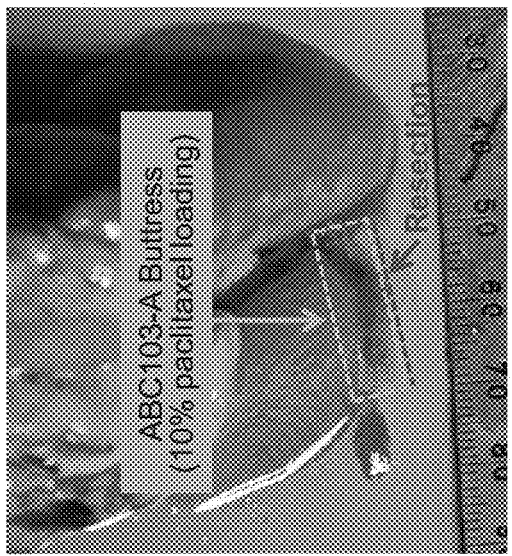
Figure 12A:
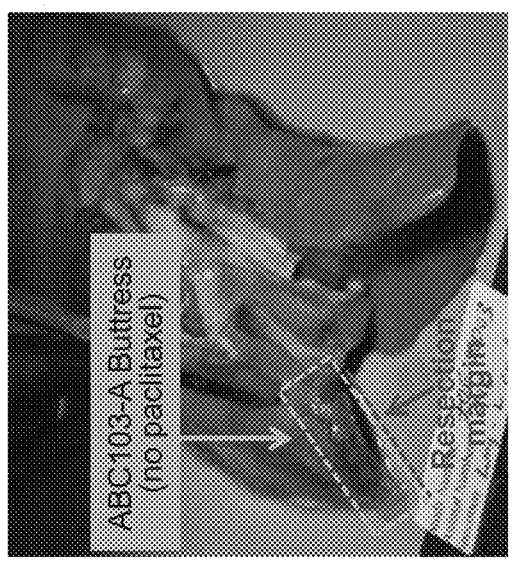
Figure 12C:
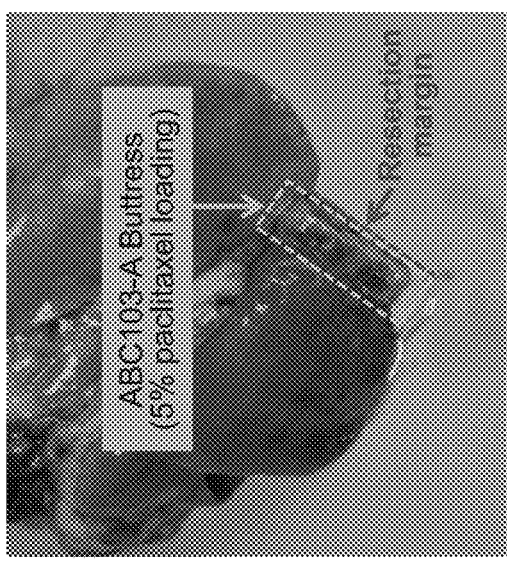

FIG. 12A-D illustrate rabbit lung tissue after 14 day affixation with ABC103-A having: no therapeutically active agent (FIG. 12A), 1% of therapeutically active agent (FIG. 12B), 5% of therapeutically active agent (FIG. 12C) and 10% of therapeutically active agent (FIG. 12D). Lungs in (FIG. 12C) and (FIG. 12D) are inflated with no leaks.

Additional dose-related in vitro release kinetics of paclitaxel from ABC103-A was as follows.

To quantify the in vitro drug release kinetics of the implants, 1 cm$^2$ ABC103-A samples were synthesized with varying paclitaxel loadings: 25 μg/cm$^2$, 120 μg/cm$^2$, 225 μg/cm$^2$ or 415 μg/cm$^2$ (1%, 5%, 10% or 20% loading, respectively). Each implant was placed in sink conditions: 100 mL of 1× phosphate buffered saline (PBS) with 2% (vol./vol.) TWEEN 80 at 37° C. with buffers replaced daily. Aliquots of the sink were taken at time points (day(s): 0.25, 1, 2, 3, 5, 7, 10, 14, 18, 23, 30) and paclitaxel quantified by LC-MS.

Figure 16:
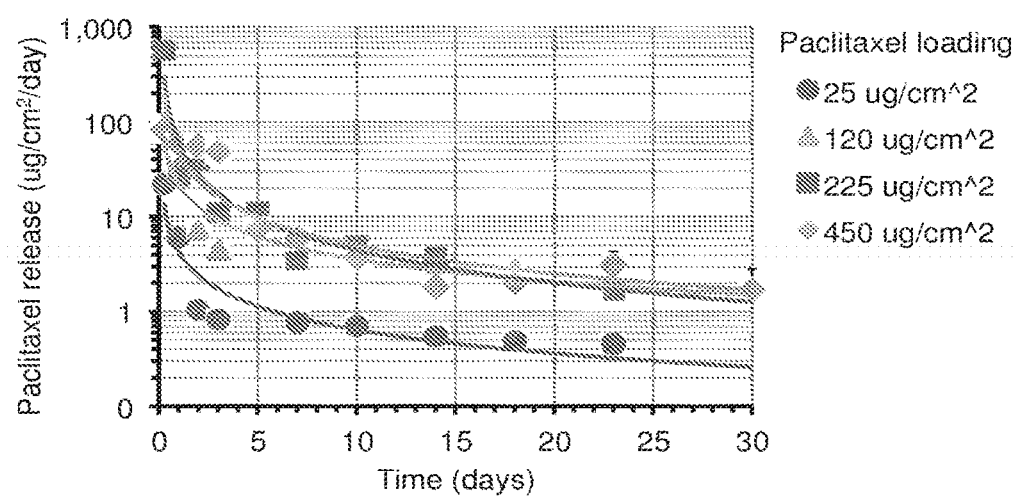
FIG. 16 illustrates the in vitro release kinetics of paclitaxel from exemplified compositions, ABC103-A.

The results demonstrated reproducible paclitaxel release kinetics from the implants. After an initial burst release on day one and two, the rate of release adopted a linear profile with no evidence of catastrophic release as a result of polymer hydrolysis (FIG. 16); outlying data were removed during analysis.

4. Drug Distribution and Safety

Animals were observed for blood leaks, air leaks, abrasion and progression of normal gross and histologic healing through day 14. Paclitaxel distribution was measured at day 14 in the organs, tissues and biological fluids.

Normal healing was observed with no gross signs of toxicity. Normal healing at the site of pulmonary resection was corroborated using histology/microscopy of fixed-stained tissues (FIG. 14A-C). FIG. 14A shows a control with uncoated buttress. Area of buttress (approximated by dashed line) with minimal surrounding fibrous connective tissue (asterisk) and mild fibrovascular tissue (double asterisks) where a. is the area of higher magnification. Note the area of buttress (within dashed line) with widespread infiltration of inflammatory cells (predominately histiocytes and multi-nucleated giant cells) and/or tissue. FIG. 14B shows a buttress as described herein without drug (paclitaxel). Note area of implant (approximated by the dashed line) with minimal surrounding fibrovascular tissue (double asterisk) where b. shows the area of higher magnification in the panel below. Note are of implant (within dashed line) with minimal infiltration of inflammatory cells and/or tissue. FIG. 14C shows the paclitaxel coated buttress loaded with 225 μg/cm$^2$ pacliataxel. Note are of implant (approximated by dashed line) with minimal surrounding fibrin (asterisk) mixed with cellular debris (double asterisk) and minimal associated inflammation or fibrovascular tissue where c. represents the area of higher magnification in the panel below. Note area of implant (within the dashed line) with minimal infiltration or inflammatory cells and/or tissue.

Figure 15:
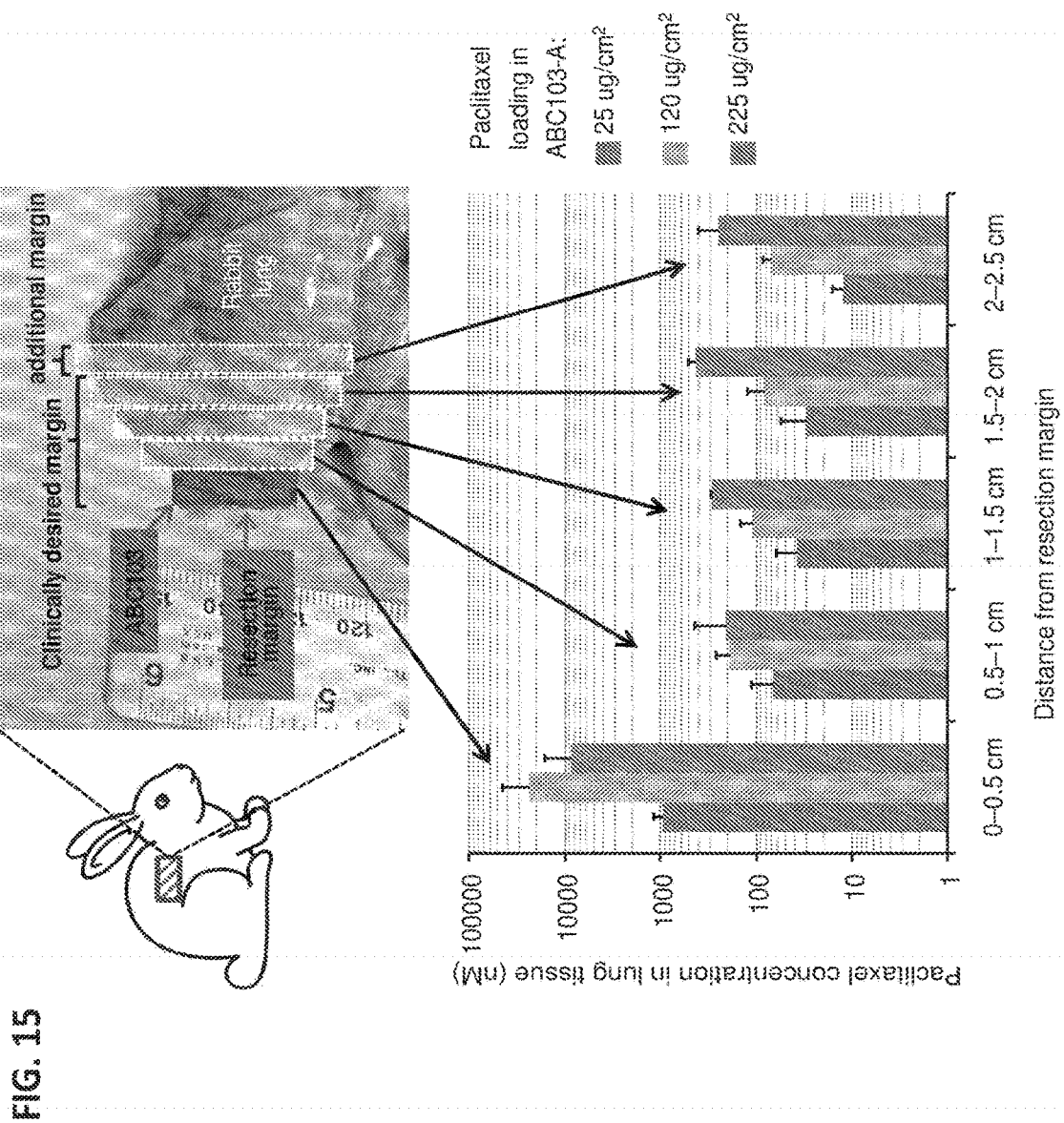
FIG. 15 illustrates the in vivo distribution of paclitaxel in rabbit lungs from an exemplified composition.

No air leaks or blood leaks were observed acutely at the time of surgery or at 14-day terminal necropsy. Paclitaxel levels in blood, pleural fluid, tissues and organs were determined. Paclitaxel levels were below quantitative limits <0.5 ng/mL in blood and tissues outside the thorax. Penetration of paclitaxel >2.5 cm away from the implant/resection margin was measured at concentrations ranging from 350 nM to 3

μM with the 225 μg/cm² loaded implant (FIG. 15). These results show that paclitaxel release kinetics from the paclitaxel-coated buttress were controlled and well tolerated in an orthotopic rabbit model.

5. Drug Distribution and Safety of Implants in the Swine Lung

ABC103-A were administered to Yorkshire pigs at 225 μg/cm² dose=~1 mg (1 cm×4.5 cm implant) and 415 μg/cm² dose=~1.9 mg (1 cm×4.5 cm implant).

Animals underwent a single surgical procedure on Day 0 in which the left cranial lobe was accessed, and two separate ABC103-A devices were applied over distal and proximal edges of the lobe and then stapled in place. Following application of buttress material, remaining distal lung tissue was resected and excess buttress material was trimmed and saved frozen for analysis, along with excess buttress material that was trimmed from the 45 mm staple site before resection. A Covidien Endo Gia stapler was used for the lung resections/buttress implants. Covidien EGIA60AMT for the distal implant (60 mm) and Covidien EGIA45AMT for the proximal implant (45 mm). Confirmation was made that no air leaks were present before closure.

Incision site observations were performed daily until healed and clinical observations were performed daily for 14 days, weekly thereafter and prior necropsy. Animals were observed for blood leaks, air leaks, abrasion and progression of normal gross and histologic healing through day 30. On Days 2, 14, 30 and 60, the animals were anesthetized and paclitaxel was measured in the blood at day 2, 14 and 30 and in the organs and tissue on day 30. The implant sites on the left lung lobe were checked for leaks and a sample of the lavage fluid was collected. Implant sites were collected, including the staple lines/implant sites, corresponding pleural areas and body wall sections. At the Day 30 and Day 60 time points, samples of the implanted lung/buttress, and at all time points samples of the pleural areas/body wall sections near the implant site were processed for histopathological evaluation. Samples for histology were fixed in 10% neutral buffered formalin. Samples that included the implanted device were resin processed and stained with Hematoxylin and Eosin (H&E) and Masson's Trichrome. Samples of non-device tissues were paraffin processed and stained with H&E. All samples for paclitaxel analysis were stored frozen at nominally −80° C.

Figure 17:
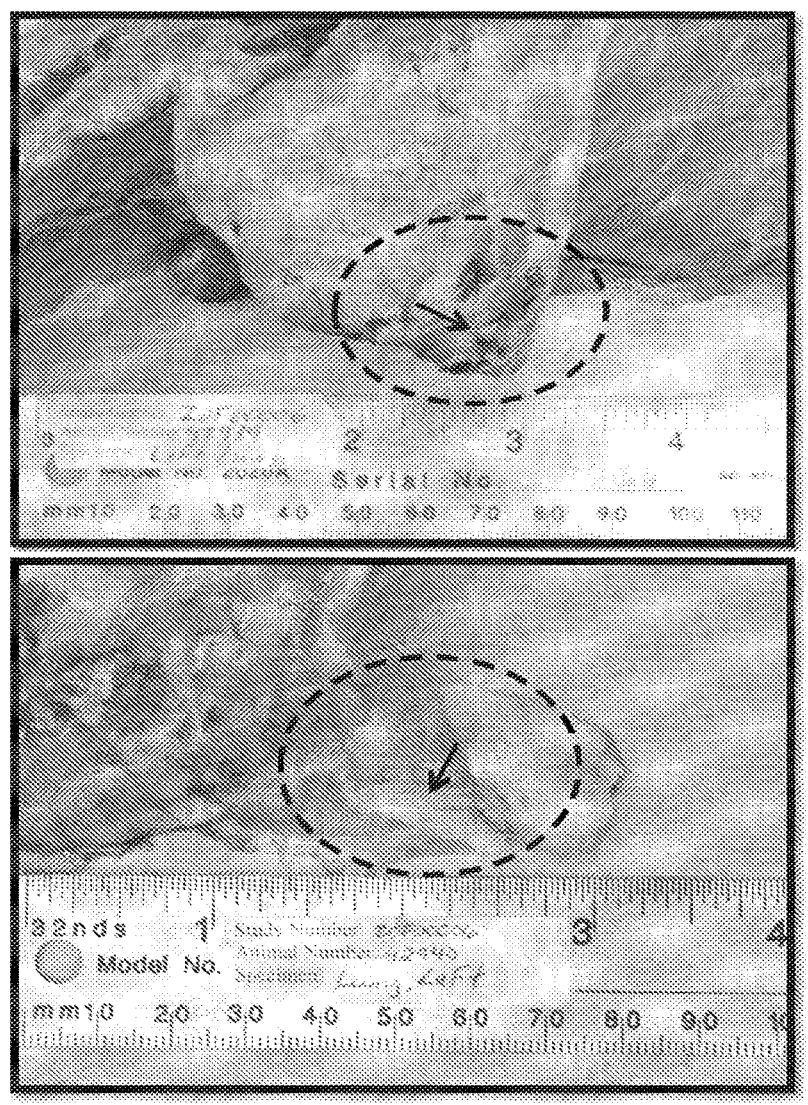
FIG. 17 illustrates the gross images of an exemplified composition and surrounding lung tissue after 30 days of implantation in pig lungs: left lung lobectomy site (within dashed circle) with the composition (arrow).
Figure 18:
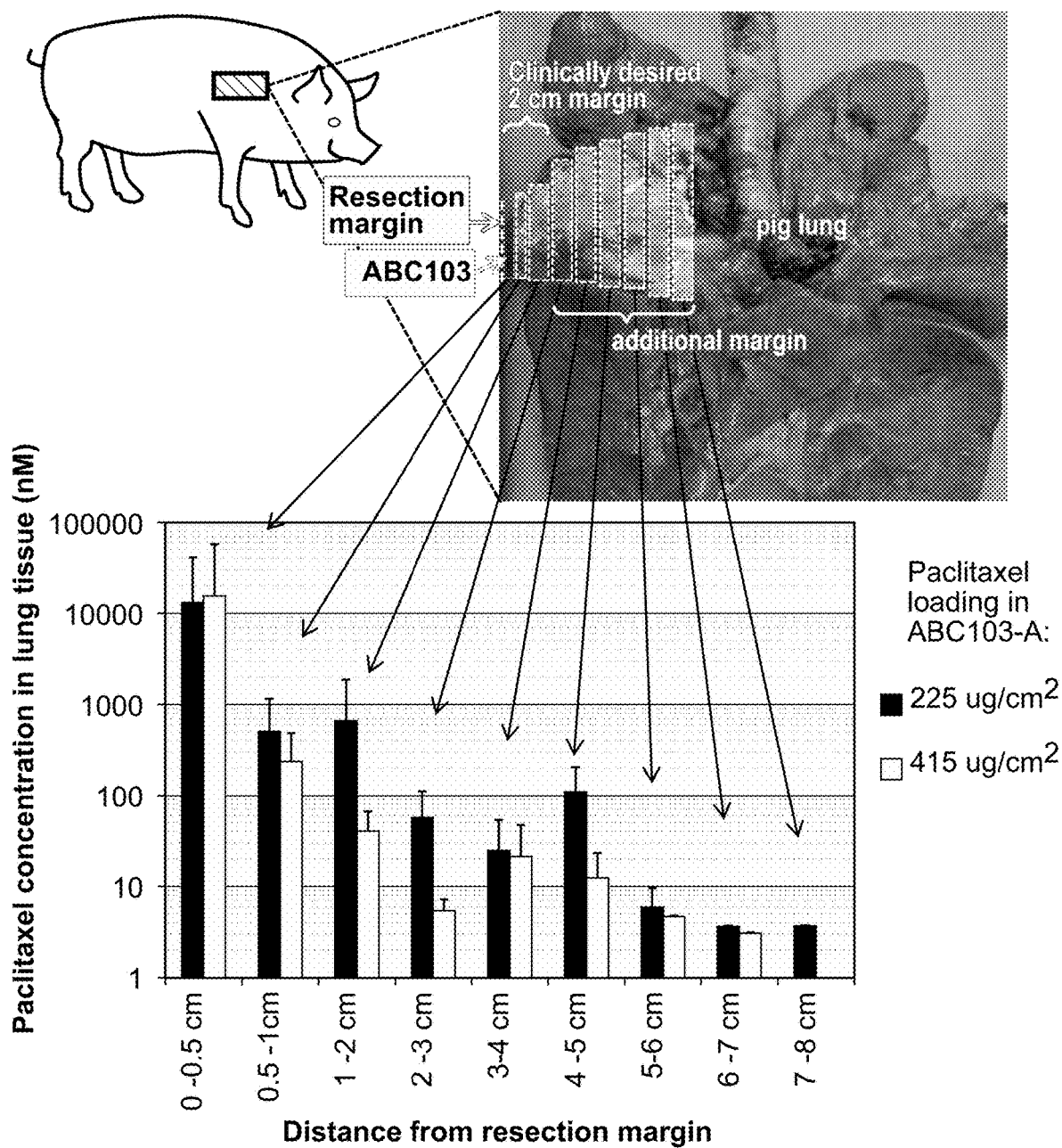
FIG. 18 illustrates the in vivo distribution of paclitaxel in pig lungs 30 days after implantation of an exemplified composition with doses of 1 mg and 1.9 mg (225 µg/cm$^2$ and 415 µg/cm$^2$, respectively).

No measurable signs of local or systemic toxicity on gross inspection or histologically with normal healing. No blood leaks, air leaks or abrasion occurred acutely or were observed at necropsy (FIG. 17). Measurable paclitaxel appeared in the treated lung and ipsilateral tracheobronchial lymph nodes with clinically relevant delivery of paclitaxel to at least 8 cm distant from the implant/resection margin at concentrations ranging from 145 nM up to 85 μM (FIG. 18). This and the 60-day data in FIG. 19A-B establish that the implants were well tolerated.

Surprisingly, measurable amounts of paclitaxel also appeared in mediastinal tissue (2.74-3.95 ng/g for 2 of 3 animals), brain (5.05 ng/g for 1 of 3 animals), thymus (2.96 ng/g for 1 of 3 animals), and kidney (2.73 ng/g for 1 of 3 animals). To date, it is believe that no other means have been reported in which a drug has been non-toxically delivered through the lymphatic system to other sites. This was unexpected and is remarkable.

Figure 20A:
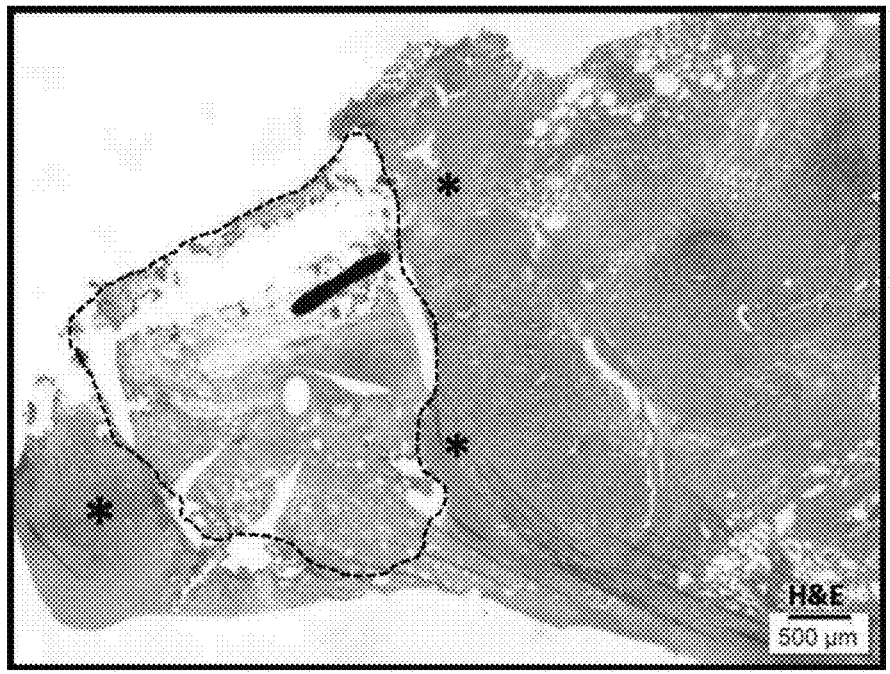
FIG. 20A-C illustrate histology of the lung 60 days after implantation with ABC103-A.
Figure 20B:
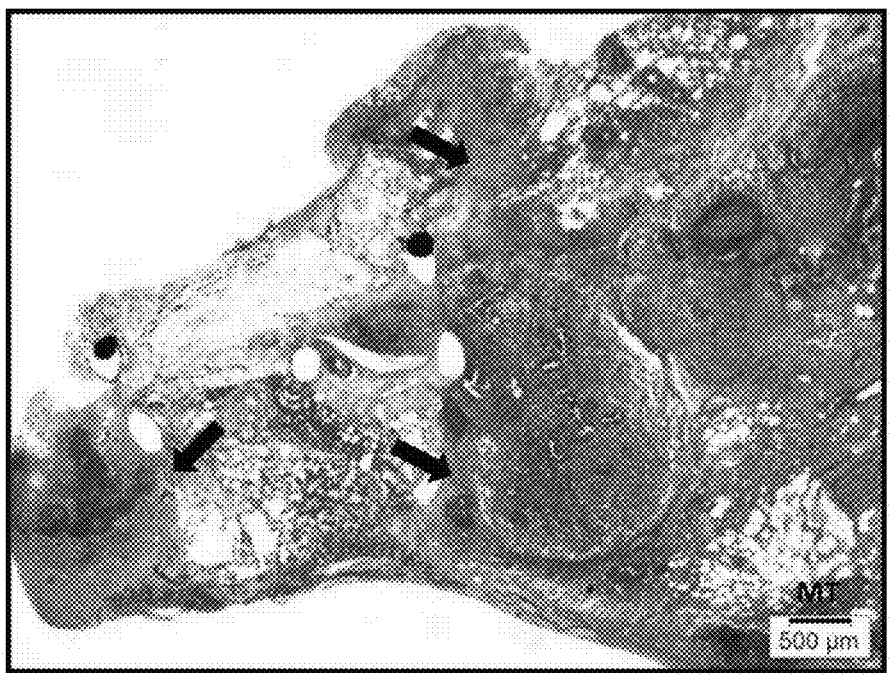
Figure 20C:
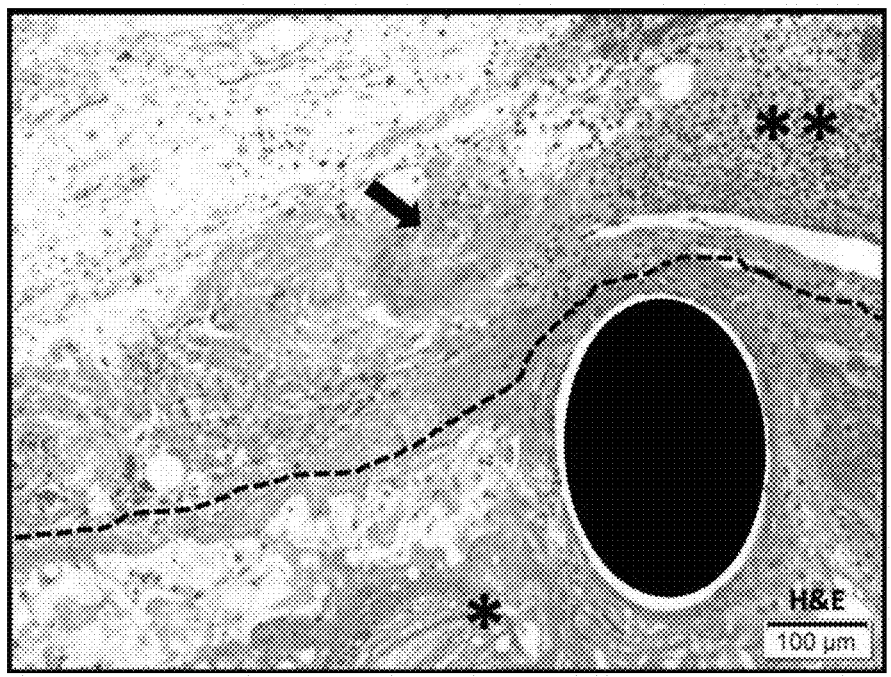

Finally, FIG. 20A-C show representative histology of the lung 60 days after implantation with ABC103-A 225 ug/cm². FIG. 20A shows H&E of lung, caudal lobe, treated with ABC103-A 225 ug/cm² 60 days following implantation. The implant is marked by the dashed line. Asterisks indicate slight consolidation and inflammation in lung areas abutting the implant area. FIG. 20B shows Masson's Trichrome (MT) staining of the section from FIG. 20A shows negligible fibrosis (arrows) at the periphery of the implant site. FIG. 20C shows the high magnification view from FIG. 20A shows fibrin (asterisk) within partially resorbed implant, mild mononuclear inflammation (double asterisk) adjacent and giant cell focus (arrow) containing slightly refractile material.

There were thoracotomy site related findings in all animals (animals that received ABC103-A 225 ug/cm2 implants and were sacrificed 2, 14, 30 or 60 days following implantation), including dark/red discoloration in all Day 2 animals, thickening and/or associated pulmonary adhesions in all Day 14 animals, and associated pulmonary adhesions in all Day 30 and Day 60 animals. Such findings are considered to be related to the surgical thoracotomy model rather than to implant presence. There were no implant-associated abrasions noted at necropsy at any time point. There was no evidence of air leakage at Day 2 or Day 14. Air leakage was present in all three Day 30 animals and one Day 60 animal. Given that pulmonary-thoracic adhesions were present, and that there was no clinical evidence of dyspnea or either macroscopic or histologic evidence of atelectasis to suggest pneumothorax, it is possible that the leakage was related to tissue disruption (i.e., breaking down of adhesions) as part of thoracic exposure during necropsy. There were no other significant macroscopic changes (e.g., necrosis, inflammation) associated with treatment sites, adjacent lung parenchyma and adjacent pleural surfaces (see FIG. 20A-C). In one Day 2 animal, there was red/dark discoloration of the lateral middle lung lobe associated with the thoracotomy site adhesion. One Day 14 animal exhibited a ~12×10 mm firm, granular, tan nodule near the treatment site, consistent with an isolated focus of fibrin or necrotic material, and typical of localized post-surgical finding.

There was no indication of adverse inflammatory reaction to implants. Mean implant associated inflammation (i.e., either within implants or along implanted surfaces of lung, as opposed to the bronchus-bronchiolar lymphoid tissue at more distant locations) was heterogeneous and minimal to mild-moderate at Day 30. Overall inflammation was slightly increased at Day 60, with minor changes in leukocyte composition, slight decreases in granulocytes (neutrophils and eosinophils) and slight increases in mononuclear cells (macrophages, giant cells and lymphocytes).

Inflammation, which was in the lobectomy regions but not directly surrounding or within implants, was generally interpreted as related to surgical model rather than device/treatment but the low sample sizes preclude definitive interpretation.

The invention claimed is:

1. An implantable composition comprising an acellular collagen matrix together with poly(lactic-co-glycolic acid) copolymer (PLGA), polyethylene glycol (PEG) 8000 and paclitaxel, wherein:
   the PLGA has a molecular weight ranging from about 20,000 g/mol to about 250,000 g/mol;
   the PLGA has a lactide/glycolide molar ratio of about 40:60 to about 60:40;
   the paclitaxel is present in an amount of 50% by weight or less based on the total weight of the PLGA and PEG 8000; and
   the PEG 8000 is present in an amount of between about 5% by weight to about 35% by weight based on the total weight of the PLGA and the paclitaxel.

2. The implantable composition of claim 1, wherein the PLGA, polyethylene glycol 8000, and paclitaxel are embedded in the matrix, coated on the matrix, and is embedded in and coated on the matrix, or covalently linked to the matrix.

3. The implantable composition of claim 2, wherein the paclitaxel is present in an amount of about 25% by weight or less of the total weight of the PLGA and polyethylene glycol 8000 embedded in the matrix, coated on the matrix, or embedded in and coated on the matrix.

4. The implantable composition of claim 1, wherein the poly(lactic-co-glycolic acid) copolymer (PLGA) has a lactide/glycolide molar ratio of about 45:55, about 53:47, about 55:45, or about 50:50.

5. The implantable composition of claim 1, wherein the poly(lactic-co-glycolic acid) copolymer (PLGA) has a molecular weight ranging from about 50,000 g/mol to about 150,000 g/mol.

6. A method of reducing the risk of acquiring a cancer in a subject in need thereof comprising surgically affixing the implantable composition of claim 1 in or on the subject.

7. The implantable composition of claim 1, wherein the PLGA has a lactide/glycolide molar ratio of about 50:50.

8. An implantable composition comprising about 25% polyethylene glycol (PEG) 8000, poly(lactic-co-glycolic acid) copolymer (PLGA) having a lactide/glycolide molar ratio of about 50:50, and paclitaxel in an amount of 50% by weight or less based on the total eight of the PLGA and PEG 8000, wherein the PEG 8000, PLGA, and paclitaxel are coated on an acellular collagen matrix.

* * * * *

UNITED STATES PATENT AND TRADEMARK OFFICE
CERTIFICATE OF CORRECTION

PATENT NO. : 10,888,530 B2
APPLICATION NO. : 15/845902
DATED : January 12, 2021
INVENTOR(S) : John Schwartz and Aaron Colby Page 1 of 1

It is certified that error appears in the above-identified patent and that said Letters Patent is hereby corrected as shown below:

In the Claims

In Claim 2, Column 25, Line number 3, please delete the phrase "and is".

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*